(12) United States Patent
Alocilja et al.

(10) Patent No.: US 10,739,337 B2
(45) Date of Patent: Aug. 11, 2020

(54) EXTRACTION AND DETECTION OF PATHOGENS USING CARBOHYDRATE-FUNCTIONALIZED BIOSENSORS

(75) Inventors: Evangelyn C. Alocilja, East Lansing, MI (US); Barbara Christine Cloutier, DeWitt, MI (US); Michael J. Anderson, Manassas, VA (US)

(73) Assignee: BOARD OF TRUSTEES OF MICHIGAN STATE UNIVERSITY, East Lansing, MI (US)

( * ) Notice: Subject to any disclaimer, the term of this patent is extended or adjusted under 35 U.S.C. 154(b) by 1517 days.

(21) Appl. No.: 13/598,160

(22) Filed: Aug. 29, 2012

(65) Prior Publication Data

US 2014/0303012 A1    Oct. 9, 2014

Related U.S. Application Data

(60) Provisional application No. 61/528,892, filed on Aug. 30, 2011.

(51) Int. Cl.
| | | |
|---|---|---|
| *G01N 33/551* | (2006.01) | |
| *G01N 33/543* | (2006.01) | |
| *G01N 33/569* | (2006.01) | |
| *G01N 27/327* | (2006.01) | |

(52) U.S. Cl.
CPC ....... *G01N 33/5434* (2013.01); *G01N 27/327* (2013.01); *G01N 33/54393* (2013.01); *G01N 33/56911* (2013.01); *G01N 27/3275* (2013.01)

(58) Field of Classification Search
CPC ......... G01N 33/5434; G01N 33/54393; G01N 33/56911
See application file for complete search history.

(56) References Cited

U.S. PATENT DOCUMENTS

| 4,486,530 A | 12/1984 | David et al. |
|---|---|---|
| 4,786,589 A | 11/1988 | Rounds |
| 4,939,096 A | 7/1990 | Tonelli |
| (Continued) | | |

OTHER PUBLICATIONS

Chumbimuni-Torres, et al., Solid Contact Potentiometric Sensors for Trace Level Measurements. Anal. Chem. (Feb. 15, 2006); 78(4): 1318-1322.

(Continued)

*Primary Examiner* — Christopher L Chin
(74) *Attorney, Agent, or Firm* — Marshall, Gerstein & Borun LLP

(57) ABSTRACT

The disclosure relates to the extraction and detection of pathogens using carbohydrate-functionalized biosensors. Immobilized carbohydrate moieties on the biosensor provide a means for non-specific binding of a plurality of target analytes. When a sample containing the target analyte is applied or otherwise transported to the biosensor detection surface, non-specific binding interactions between the carbohydrate moiety and the analyte immobilize/retain the analyte at the detection surface. The carbohydrate moiety is a stable binding pair member that allows on-sensor rinsing of a sample to enhance detection of an analyte in the sample. Specific analyte identification can be achieved with an analyte probe having a detection moiety and a binding pair member specific to the target analyte of interest.

22 Claims, 8 Drawing Sheets

(56) References Cited

U.S. PATENT DOCUMENTS

| | | |
|---|---|---|
| 4,965,187 A | 10/1990 | Tonelli |
| 5,166,078 A | 11/1992 | McMahon et al. |
| 5,169,789 A | 12/1992 | Bernstein |
| 5,177,014 A | 1/1993 | O'Connor et al. |
| 5,219,725 A | 6/1993 | O'Connor et al. |
| 5,256,372 A | 10/1993 | Brooks et al. |
| 5,312,762 A | 5/1994 | Guiseppi-Elie |
| 5,356,785 A | 10/1994 | McMahon et al. |
| 5,491,097 A | 2/1996 | Ribi et al. |
| 5,518,892 A | 5/1996 | Naqui et al. |
| 5,536,644 A | 7/1996 | Ullman et al. |
| 5,559,041 A | 9/1996 | Kang et al. |
| 5,620,845 A | 4/1997 | Gould et al. |
| 5,620,895 A | 4/1997 | Naqui et al. |
| 5,627,026 A | 5/1997 | O'Connor et al. |
| 5,656,448 A | 8/1997 | Kang et al. |
| 5,670,031 A | 9/1997 | Hintsche et al. |
| 5,695,928 A | 12/1997 | Stewart et al. |
| 5,700,655 A | 12/1997 | Croteau et al. |
| 5,726,010 A | 3/1998 | Clark |
| 5,726,013 A | 3/1998 | Clark |
| 5,728,587 A | 3/1998 | Kang et al. |
| 5,750,333 A | 5/1998 | Clark |
| 5,753,456 A | 5/1998 | Naqui et al. |
| 5,976,896 A | 11/1999 | Kumar et al. |
| 5,985,594 A | 11/1999 | Croteau et al. |
| 6,057,165 A * | 5/2000 | Mansour .......... G01N 33/54366 422/401 |
| 6,136,554 A | 10/2000 | Bochner |
| 6,315,926 B1 | 11/2001 | Jansen |
| 6,331,356 B1 | 12/2001 | Angelopoulos et al. |
| 6,333,145 B1 | 12/2001 | Cloots et al. |
| 6,333,425 B1 | 12/2001 | Michot et al. |
| 6,468,809 B1 * | 10/2002 | Prinz .................... G01N 27/745 209/214 |
| 6,478,938 B1 | 11/2002 | Peek et al. |
| 6,733,655 B1 * | 5/2004 | Davies ................ C12Q 1/001 205/775 |
| 7,541,004 B2 | 6/2009 | Niksa et al. |
| 2003/0040129 A1 * | 2/2003 | Shah .................. B01L 3/5027 506/32 |
| 2003/0153094 A1 * | 8/2003 | Alocilja ............ G01N 33/5438 436/516 |
| 2003/0170613 A1 | 9/2003 | Straus |
| 2003/0178309 A1 | 9/2003 | Huang et al. |
| 2004/0023412 A1 * | 2/2004 | Carlsson .......... G01N 33/54386 436/514 |
| 2004/0105980 A1 * | 6/2004 | Sudarshan ......... C10M 171/001 428/404 |
| 2005/0009002 A1 | 1/2005 | Chen et al. |
| 2006/0292636 A1 * | 12/2006 | Yarnall ............. C07K 16/1232 435/7.1 |
| 2007/0020700 A1 | 1/2007 | Carpenter et al. |
| 2008/0193965 A1 | 8/2008 | Zeng et al. |
| 2008/0241964 A1 * | 10/2008 | Kaieda ............ G01N 33/54333 436/526 |
| 2008/0305963 A1 | 12/2008 | Alocilja et al. |
| 2008/0314766 A1 | 12/2008 | Alocilja et al. |
| 2009/0123939 A1 | 5/2009 | Alocilja et al. |
| 2009/0181441 A1 * | 7/2009 | Jin .......................... C12N 11/08 435/180 |
| 2010/0075432 A1 * | 3/2010 | Piletsky .............. A61B 5/4821 436/131 |
| 2011/0171749 A1 | 7/2011 | Alocilja et al. |

OTHER PUBLICATIONS

Cloutier et al., Validation of the M3 Biosensor for Extraction and Detection of *Escherichia coli* O157:H7 in Broth, Nano DDS Conference (Aug. 30, 2011).

Dubus et al., PCR-Free DNA Detection Using a Magnetic Bead-Supported Polymeric Transducer and Microelectromagnetic Traps. Anal. Chem. (Jul. 1, 2006); 78(13): 4457-4464.

Farace et al., Reagentless Biosensing Using Electrochemical Impedance Spectroscopy. Bioelectrochemistry (Jan. 2002): 55(1-2):1-3.

Houseman et al., Carbohydrate Arrays for the Evaluation of Protein Binding and Enzymatic Modification, Chem. & Bio. v9, 443-454, (2002).

Kim et al., Conductimetric Membrane Strip Immunosensor with Polyaniline-Bound Gold Colloids as Signal Generator. Bio and Bioelectronics (Feb. 2000); 14(12): 907-915.

Luo et al., s-Electron Ferromagnetism in Gold and Silver Nanoclusters. Nano Letters (Oct. 2007); 7(1): 3134-3137.

Muhammad-Tapir et al., (2003b), Fabrication of a Disposable Biosensor for *Escherichia coli* 0157:H7 Detection. IEEE Sensor Journal, 3(4), 345-351.

Pal et al., Nanowire Labeled Direct-Charge Transfer Biosensor for Detecting *Bacillus* Species, Biosens Bioelectron, vol. 22, pp. 2329-36, 2007.

Park, et al., Array-Based Electrical Detection of DNA with Nanoparticle Probes. Sci. (Feb. 2002); 295(5559): 1503-1506.

Poddar et al., Magnetic Properties of Conducting Polymer Doped with Manganese-Zinc Ferrite Nanoparticles. Nanotechnology (Oct. 2004); 15(10): S570-S574.

Rosi, et al., Nanostructures in Biodiagnostics. Chem. Reviews (Apr. 2005); 105(4): 1547-1562.

Schwarz et al., A New Kind of Carbohydrate Array, Its Use for Profiling Antiglycan Antibodies, and the Discovery of a Novel Human Cellulose-Binding Antibody, Glycobiology, v13, No. 11, pp. 749-754 (2003).

Setterington et al., Magnetic/Polyaniline Core/Shell Nanoparticles for Target Extraction and Electrical Detection of Threat-Agents, Nano-DDS 2009 presentation (Sep. 29, 2009).

Setterington et al., Immunomagnetic Extraction and Magnet-Aided Electrochemical Detection of Polyaniline-Labeled Bacterial Cells, Biosensors 2010 presentation (May 26, 2010).

Setterington et al., Rapid Electrochemical Detection of Polyaniline-labeled *Escherichia coli* O157:H7, (2011) 26, 2208-2214 (available online Sep. 25, 2010).

Sharma et al., Composition Dependent Magnetic Properties of Iron Oxide-Polyaniline Nanoclusters, Journal of Applied Physics 97, 014311(2005).

Stejskal J., Polyaniline. Preparation of a Conducting Polymer, Pure Appln. Chem., vol. 74, No. 5, pp. 857-867 (2002).

Zhu et al., Electrochemically Fabricated Polyaniline Nanowire-Modified Electrode for Voltammetric Detection of DNA Hybridization. Electro. Acta, 51, (2006) 3758-3762.

\* cited by examiner

EXTRACTION AND DETECTION OF PATHOGENS USING CARBOHYDRATE-FUNCTIONALIZED BIOSENSORS

CROSS REFERENCE TO RELATED APPLICATION

Priority is claimed to U.S. Provisional Application No. 61/528,892, filed Aug. 30, 2011, the entire content of which is incorporated herein by reference in its entirety.

STATEMENT OF GOVERNMENT INTEREST

This invention was made with government support from the Department of Homeland Security through the National Center for Food Protection and Defense under grant number X9106025105. The government has certain rights in the invention.

BACKGROUND OF THE DISCLOSURE

Field of the Disclosure

The disclosure generally relates to the extraction and detection of pathogens using carbohydrate-functionalized biosensors. Immobilized carbohydrate moieties on the biosensor provide a means for non-specific binding of a plurality of target analytes. Specific analyte identification can be achieved with an analyte probe having a detection moiety and a binding pair member specific to the target analyte of interest.

Brief Description of Related Technology

Statistics has shown that pathogens result in an estimated 14 million illnesses, 60,000 hospitalizations, 1,800 deaths, and cost approximately $2.9-$6.7 billion in the United States each year due to food-borne diseases (e.g., resulting from infection by *Escherichia coli* O157:H7). The U.S. Centers for Disease Control and Prevention (CDC) and the National Institute of Allergy and Infectious Diseases (NIAID) classify *E. coli* O157:H7 as a Category B (i.e., second highest priority) pathogen for biodefense, because of its ease of transmission and dissemination in water and food sources. Furthermore, possible bioterror threats have generated urgent needs of biosensors for surveillance of foods to prevent the contamination of food supplies. Of these numerous food-borne pathogens, *Bacillus cereus* has garnered notice as bacteria that can cause two types of food poisoning: a diarrheal type, and an emetic type. The former leads to diarrhea while the latter results in vomiting. The ubiquitous nature of the *Bacillus cereus* pathogen is demonstrated by its status as a common soil saprophyte and association with foods, primarily plants, but also meats, eggs, and dairy products. It was implicated in a third of all cases of food poisoning in Norway (1988-1993), 47% in Iceland (1985-1992), and 22% in Finland (1992). Furthermore, recent research has concluded that *Bacillus anthracis* and *Bacillus cereus* are of the same species. *B. anthracis* is responsible for the lethal disease anthrax, an agent in biological terrorism/warfare. Thus, detection and defense against *B. cereus* may accurately model and lead to heightened security with respect to *B. anthracis*.

Identification of pathogens by conventional methods, however, necessitates manual work and anywhere from 24 to 48 hours of incubation time. Thus, there exists a need for improved methods and compositions useful for the rapid, accurate, and selective detection of various pathogens.

Detection technologies employing magnetic particles or microbeads have been used. These particles bind with the target analyte in a sample being tested, for example using a binding pair member specific to the target analyte, and are then typically isolated or separated out of solution magnetically. Once isolation has occurred, other testing may be conducted to detect the presence of analyte-bound particles. For example, various types of immunoassays based upon detecting a signal from a capture reagent are described in U.S. Pat. No. 5,620,845 to Gould et al.; U.S. Pat. No. 4,486,530 to David et al.; U.S. Pat. No. 5,559,041 to Kang et al.; U.S. Pat. No. 5,656,448 to Kang et al.; U.S. Pat. No. 5,728,587 to Kang et al.; U.S. Pat. No. 5,695,928 to Stewart et al.; U.S. Pat. No. 5,169,789 to Bernstein et al.; U.S. Pat. Nos. 5,177,014, 5,219,725, and 5,627,026 to O'Conner et al.; U.S. Pat. No. 5,976,896 to Kumar et al.; U.S. Pat. Nos. 4,939,096 and 4,965,187 to Tonelli; U.S. Pat. No. 5,256,372 to Brooks et al.; U.S. Pat. Nos. 5,166,078 and 5,356,785 to McMahon et al.; U.S. Pat. Nos. 5,726,010, 5,726,013, and 5,750,333 to Clark; U.S. Pat. Nos. 5,518,892, 5,753,456, and . 5,620,895 to Naqui et al.; U.S. Pat. Nos. 5,700,655 and 5,985,594 to Croteau et al.; and U.S. Pat. No. 4,786,589 to Rounds et al. The aforementioned U.S. patents are hereby incorporated herein by reference herein in their entireties.

Alocilja et al. U.S. Publication Nos. 2003/0153094, 2008/0314766, 2009/0123939, and 2011/0171749 generally relate to biosensor devices, biologically enhanced, electrically active magnetic (BEAM) nanoparticle compositions, and/or other nanoparticle compositions for pathogen detection and are incorporated herein by reference in their entireties.

SUMMARY

In one aspect, the disclosure relates to a method for detecting the presence of a target analyte, the method comprising: (a) providing an analyte conjugate comprising: (i) a target analyte, (ii) a specific binding pair member bound to the target analyte, the specific binding pair member being capable of specifically binding to the target analyte, and (iii) a detection moiety bound to the specific binding pair member; (b) providing a biosensor comprising a non-specific binding pair member immobilized on a detection surface of the biosensor, the non-specific binding pair member comprising a carbohydrate moiety capable of non-specific binding to the target analyte; (c) immobilizing the analyte conjugate on the detection surface of the biosensor; (d) detecting the detection moiety of the immobilized analyte conjugate; and (e) optionally determining that the target analyte is present in a sample from which the analyte conjugate is formed. In a refinement, providing an analyte conjugate comprises: (i) providing a sample comprising the target analyte; (ii) providing an analyte probe comprising the specific binding pair member and the detection moiety bound to the specific binding pair member; (iii) contacting the analyte probe with the sample under conditions sufficient to specifically bind the specific binding pair member to the target analyte, thereby forming the analyte conjugate; and (iv) optionally separating the analyte conjugate from the sample prior to immobilizing the analyte conjugate on the detection surface of the biosensor (e.g., immunomagnetic separation, rinsing, concentration). In another refinement directed to the multiplexed analysis of different target analytes in a sample or samples using biosensors with the same type of carbohydrate functionalization, the method further comprises replicating steps (a)-(d) in a multiplexed analysis for the detection of a plurality of different target analytes in a sample, wherein: (i) the target analyte, the specific binding pair member bound to the target analyte, and the corresponding analyte conjugate formed therefrom are different for each sample replicate in the multiplexed analysis; and (ii) the biosensor comprises the same carbohydrate moiety or moieties for each sample replicate in the multiplexed analysis.

In another aspect, the disclosure relates to a kit for binding a target analyte, the kit comprising: (a) an analyte probe comprising: (i) a specific binding pair member capable of specifically binding to a target analyte, and (ii) a detection moiety bound to the specific binding pair member; and (b) a biosensor comprising a non-specific binding pair member immobilized on a detection surface of the biosensor, the non-specific binding pair member comprising a carbohydrate moiety capable of non-specific binding to the target analyte. In a refinement, (i) the kit comprises a plurality of analyte probes, each analyte probe comprising a specific binding pair member capable of specifically binding to a different target analyte; and/or (ii) the carbohydrate moiety is capable of non-specific binding to each of the different target analytes of the analyte probes. In another refinement, (i) the detection moiety of the analyte conjugate comprises conductive polymer nanoparticle, the specific binding pair member being bound to the conductive polymer nanoparticle; and (ii) the kit further comprises a magnetic nanoparticle capture composition comprising: (A) a magnetic nanoparticle, and (B) an additional specific binding pair member bound to the magnetic nanoparticle, the additional specific binding pair member being capable of specifically binding to the target analyte. In another refinement, (i) the detection surface of the biosensor has opposing top and bottom surfaces, where the non-specific binding pair member is immobilized on the top surface; and (ii) the biosensor further comprises a magnetic means for generating a magnetic field positioned adjacent the bottom surface of the detection surface.

In another aspect, the disclosure relates to a target analyte complex comprising: (a) a target analyte; (b) a specific binding pair member bound to the target analyte, the binding pair member being capable of specifically binding to the target analyte; (c) a detection moiety bound to the specific binding pair member; and (d) a non-specific binding pair member bound to the target analyte, the non-specific binding pair member comprising a carbohydrate moiety capable of non-specific binding to the target analyte.

Various refinements and extensions of the foregoing methods, kits, and compositions are possible. For example, the carbohydrate moiety can comprise a mannose moiety. More generally, the carbohydrate moiety can comprise at least one of a glucose moiety, a galactose moiety, a fucose moiety, a N-acetylgalactosamine moiety, a N-acetylglucosamine moiety, a mannose moiety, a rhamnose moiety, a N-Acetylneuraminic acid moiety, a glucuronic acid moiety, a galacturonic acid moiety, an arabinofuranose acid moiety, and a xylose moiety (e.g., alone as a monosaccharide; together with the same or other saccharide moieties in an oligo- or polysaccharide), The carbohydrate moiety can be selected from the group consisting of monosaccharides, glycosides thereof, and combinations thereof. The non-specific binding pair member can be immobilized on the detection surface via a stable covalent bond. The biosensor can be a screen-printed carbon electrode (SPCE), and the detection surface can be a working electrode of the SPCE. The target analyte can comprise a bacterium, for example where (i) the bacterium is selected from the group consisting of *Escherichia, Bacillus, Staphylococcus, Klebsiella, Shigella, Pseudomona, Vibrio, Enterobacter*, species of the foregoing genera, and strains of the foregoing; (ii) the specific binding pair member is capable of specifically binding to the selected bacterium; and (iii) the carbohydrate moiety is capable of non-specific binding to a plurality of bacteria from the group. Immobilizing the analyte conjugate can comprise contacting the analyte conjugate with the detection surface of the biosensor under conditions sufficient to non-specifically bind the carbohydrate moiety to the target analyte of the analyte conjugate. The detection surface can be washed with the analyte conjugate immobilized thereon and prior to detecting the detection moiety. The detection moiety of the analyte conjugate can comprise a conductive polymer moiety. Prior to detecting the detection moiety, the conductive polymer moiety of the analyte conjugate can be electrically activated, thereby forming an electrically activated analyte conjugate having an increased electrical conductivity relative to the analyte conjugate. Detecting the detection moiety can comprise conductimetrically or electrochemically detecting the conductive polymer moiety of the analyte conjugate. For example, the analyte conjugate can be immobilized on a working electrode and adjacent a counter/reference electrode of an electrochemical biosensor device for performing conductimetric or electrochemical detection, or the analyte conjugate can be immobilized on a detection surface and between opposing electrodes of an electrochemical biosensor device for performing conductimetric or electrochemical detection. In a refinement, the detection moiety of the analyte conjugate can comprise a conductive polymer shell bound to a magnetic nanoparticle core, the specific binding pair member being bound to the conductive polymer shell, such as where (i) the magnetic nanoparticle comprises at least one of Fe(II) and Fe(III); and, (ii) the conductive polymer is selected from the group consisting of polyanilines, polypyrroles, polythiophenes, derivatives thereof, combinations thereof, blends thereof with other polymers, and copolymers of the monomers thereof. In another refinement, (i) the detection moiety of the analyte conjugate comprises conductive polymer nanoparticle, the specific binding pair member being bound to the conductive polymer nanoparticle; and (ii) the analyte conjugate further comprises a magnetic nanoparticle capture composition comprising: (A) a magnetic nanoparticle, and (B) an additional specific binding pair member bound to the magnetic nanoparticle and bound the target analyte, the additional specific binding pair member being capable of specifically binding to the target analyte. In an embodiment, (i) the detection surface of the biosensor has opposing top and bottom surfaces, where the analyte conjugate is immobilized on the top surface; (ii) the biosensor further comprises a magnetic means for generating a magnetic field positioned adjacent the bottom surface of the detection surface; (iii) the analyte conjugate further comprises a magnetic moiety separately conjugated to the target analyte or bound to the detection moiety of the analyte conjugate; and (iv) immobilizing the analyte conjugate on the detection surface of the biosensor comprises (A) generating the magnetic field with the magnetic means to magnetically position the analyte conjugate closer to the top surface of the detection surface than in the absence of the magnetic field, and (B) maintaining the magnetic field when detecting the detection moiety in part (d) (e.g., on an electrode detection surface such as the working electrode of an SPCE). In a refinement, the detection surface can be washed with the analyte conjugate immobilized thereon in the absence of a magnetic field and prior to generating the magnetic field with the magnetic means.

Additional features of the disclosure may become apparent to those skilled in the art from a review of the following detailed description, taken in conjunction with the drawings, examples, and appended claims.

BRIEF DESCRIPTION OF THE DRAWINGS

For a more complete understanding of the disclosure, reference should be made to the following detailed description and accompanying drawings wherein.

Figure 1A:
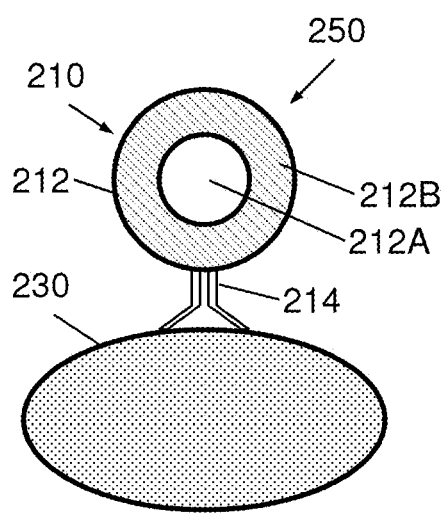
FIGS. 1A and 1B illustrate analyte conjugates for analyte detection using carbohydrate functionalized biosensors according to the disclosure (1A: one-particle analyte probe with combined detection and separation moieties; 1B: two-particle analyte probe with separate detection and separation moieties).

While the disclosed compositions, methods, and kits are susceptible of embodiments in various forms, specific embodiments of the disclosure are illustrated in the drawings (and will hereafter be described) with the understanding that the disclosure is intended to be illustrative, and is not intended to limit the claims to the specific embodiments described and illustrated herein.

DETAILED DESCRIPTION

The disclosure generally relates to the extraction and detection of pathogens using carbohydrate-functionalized biosensors. Immobilized carbohydrate moieties on the biosensor provide a means for non-specific binding of a plurality of target analytes (e.g., different genera, species, and/or strains of bacteria). Specific analyte identification can be achieved with an analyte probe having a detection moiety and a binding pair member specific to the target analyte of interest (e.g., a biologically enhanced, electrically active magnetic (BEAM) nanoparticle composition as described below or otherwise).

The carbohydrate moiety is generally immobilized on a detection surface of a biosensor. When a sample containing the target analyte is applied or otherwise transported to the biosensor detection surface (e.g., by direct application or indirect application such as in a lateral flow assay), non-specific binding interactions between the carbohydrate moiety and the analyte immobilize/retain the analyte at the detection surface. The carbohydrate moiety is a stable binding pair member (e.g., stable over extended storage periods such as at room temperature) that further allows on-sensor rinsing of a sample to enhance detection of any analyte within the sample by removal of non-target interferences or other sample constituents without substantial removal or loss of the target analyte (i.e., due to its immobilization).

A particulate composition formed from a conductive polymer (e.g., conductive polyanilines) bound to magnetic nanoparticles (e.g., $\gamma$-$Fe_2O_3$) is disclosed as a platform for the analyte probe. The particulate composition is alternatively referenced as an electrically-active magnetic ("EAM") nanoparticle composition. The particulate composition can be formed into a biologically enhanced, electrically active magnetic (BEAM) nanoparticle composition by further including a specific binding pair member (e.g., an antibody or a fragment thereof that specifically recognizes an analyte such as a specific species or strain of bacteria) bound to the conductive polymer of the particulate composition. The BEAM nanoparticle composition can be used as an analyte probe in combination with the carbohydrate-functionalized biosensor. In particular embodiments, the disclosure provides compositions, kits, detection apparatus, and methods for detecting a specific pathogen alone or for detecting a plurality of different particular pathogens in a multiplexed configuration. The disclosed compositions and methods are useful for the rapid, accurate, and selective detection of various pathogens using a biosensor platform that is shelf-stable and capable of non-selective binding to multiple analytes in a class encompassing the specific pathogen(s) of interest, such as in assays exploiting the magnetic properties of the nanoparticle compositions (e.g., for analyte concentration) and using any of a variety of detection mechanisms (e.g., conductimetric detection, magnetic detection, using an enzyme label for colorimetric detection).

The BEAM nanoparticle composition can perform a dual function of a magnetic concentrator and a transducer in biosensing applications. The magnetic properties of the BEAM nanoparticles serve the purpose of concentrating and separating specific target analytes from complex sample matrices, while the electrical properties of the BEAM nanoparticles can be exploited in various detection schemes, for example biosensing applications which can be based on a conductimetric or other suitable type of assay (e.g., with the conductive polymer serving as the detection moiety).

These EAM nanoparticle compositions can mimic the function of magnetic beads widely used as a separator for immunomagnetic separation in immunoassays, for hybridization with nucleic acid probes as capture reagents, as templates in PCR, and the like. In addition, the electrical and the magnetic properties of the nanoparticles or composites can also be exploited as molecular transducers in biosensors. Some of the major advantages of the compositions include: (1) ability to perform the dual function of a magnetic concentrator as well as a biosensor transducer; (2) ability to achieve faster assay kinetics since the compositions are in suspension and in close proximity to target analytes; (3) increased surface area for the biological events to occur; (4) minimized matrix interference due to the improved separation and washing steps; (5) ability to magnetically manipulate the magnetic nanomaterials by using permanent magnets or electromagnets; (6) ability to avoid complex pre-enrichment, purification or pre-treatment steps necessary in standard methods of detection; (7) ability to design cheap, sensitive, highly specific and rapid detection devices for diverse targets by using different biological modifications; and (8) ability to design different rapid detection devices using both electrical and magnetic properties of the BEAM nanoparticles.

Carbohydrate-Functionalized Biosensor

Figure 1B:
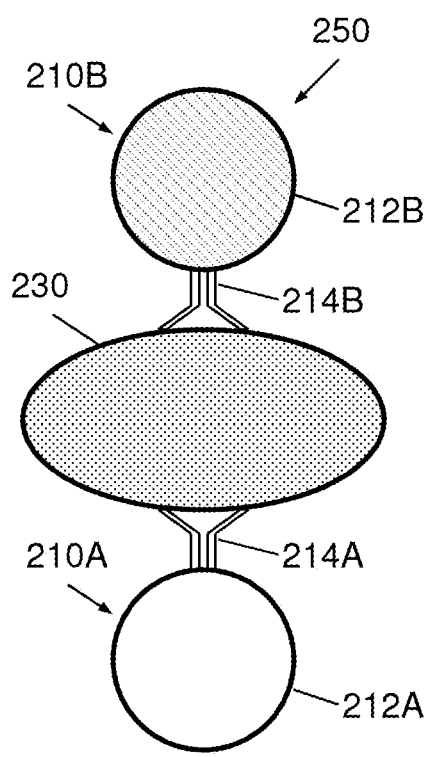
Figure 2A:
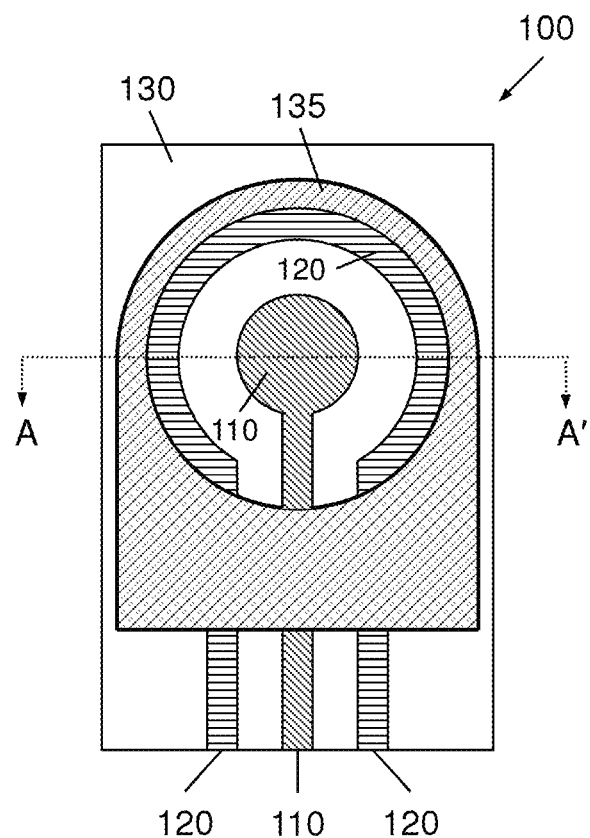
FIG. 2A illustrates a top view of a biosensor suitable for carbohydrate functionalization and pathogen detection according to the disclosure.
Figure 2B:
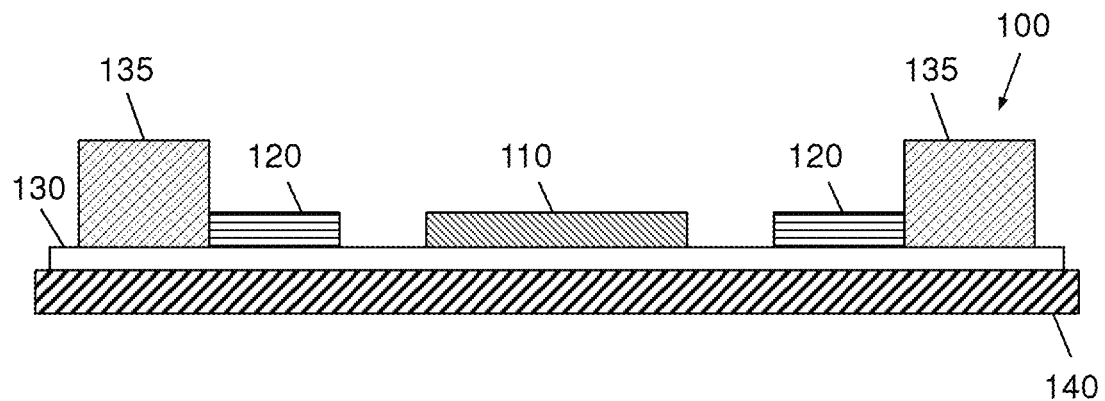
FIGS. 2B-2E illustrate side cross-sectional views (view A-A' from FIG. 2A) of a functionalized biosensor including a non-specific carbohydrate binding moiety according to the disclosure and at various stages of functionalization/pathogen detection (2B: non-functionalized biosensor; 2C: functionalized biosensor; 2D: functionalized biosensor after application of analyte conjugates thereto; 2E functionalized biosensor after rinsing of excess analyte probes therefrom).
Figure 2C:
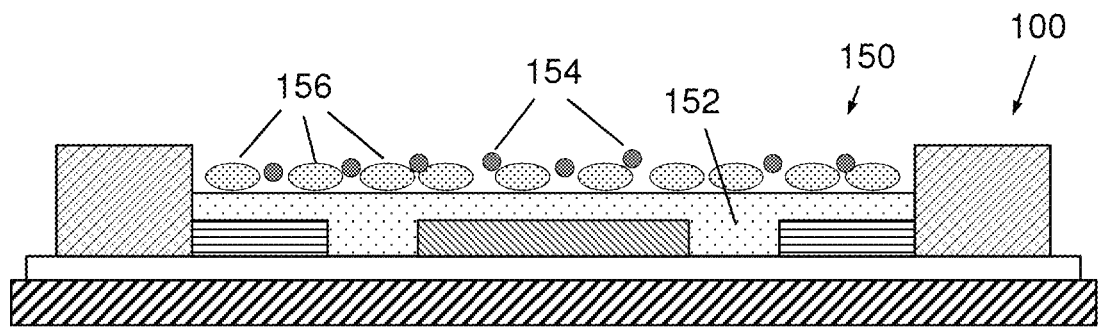
Figure 2D:
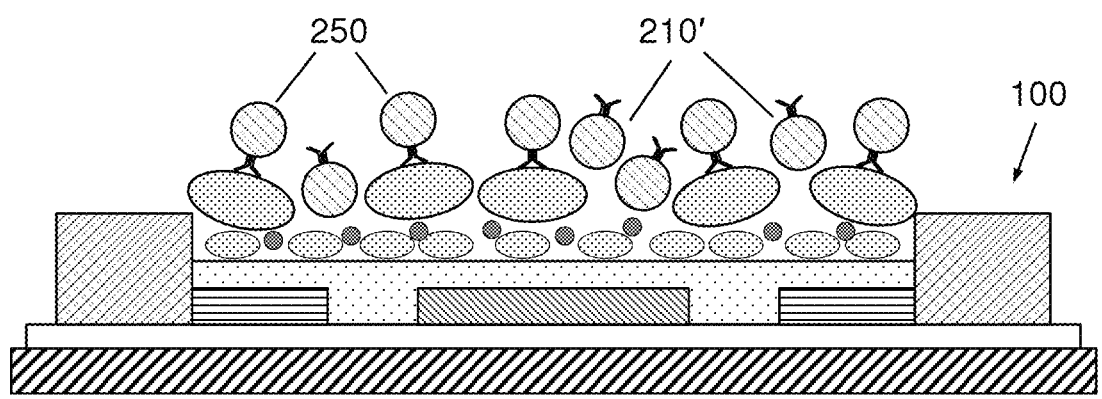
Figure 2E:
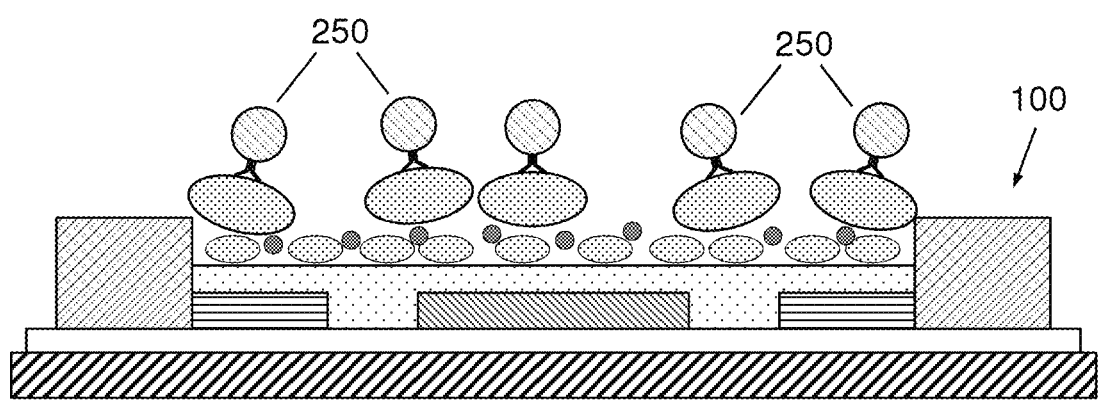

The disclosure relates to a carbohydrate-functionalized biosensor. FIGS. 2A-2E illustrate a biosensor 100 (e.g., a screen-printed carbon electrode (SPCE) as shown) for detection of an analyte conjugate 250 (FIGS. 1A and 1B). The illustrated biosensor 100 includes a working electrode 110 as a detection surface and a counter/reference electrode 120 (FIGS. 2A and 2B). The biosensor 100 further can include a dielectric or other material 135 to define a biosensor working area (e.g., for sample/analyte conjugate application, analyte detection). The biosensor 100 components/electrodes are suitably mounted upon any desired substrate 130 (e.g., polyester, polyvinylchloride, or other solid material). In some embodiments, the biosensor 100 includes a magnet 140 (e.g., electromagnet that can be powered on and off) mounted below the substrate 130 on a surface opposite the biosensor 100 components/electrodes. The magnet 140 can be used to attract a magnetic portion of an analyte probe/conjugate 210/250 toward the electrode surfaces 110, 120, thereby enhancing the electrical sensitivity of the biosensor 100 (e.g., due to the closer proximity of the electrically conductive portion of the probe/conjugate 210/250). The detection surface 110 includes a carbohydrate-functionalized surface 150 for immobilization of the analyte conjugate 250 (FIGS. 2C-2E). The carbohydrate-functionalized surface 150 includes a carbohydrate moiety 156 as a component, and it can further include an immobilization means or layer 152 for immobilization of the carbohydrate moiety 156 (e.g., illustrated as a glutaraldehyde layer 152) and/or other functional biosensor components 154 (e.g., illustrated as gold nanoparticles 154 to enhance conductivity in a conductimetric biosensor).

The specific type of biosensor is not particularly limited and generally includes devices known and used for the detection of an analyte or target DNA molecule by combining a biological component (e.g., biological material such as tissue, microorganisms, organelles, cell receptors, enzymes, antibodies, nucleic acids, probe DNA, biomimic, etc.) with a physicochemical transducer element (e.g., an element that works in a physicochemical way; optical, electrical, piezoelectric, electrochemical, etc.) that transforms the signal resulting from the interaction of the analyte with the biological element into another signal (i.e., transducers) that can be measured and quantified. In some embodiments, the transducers act as a means for amplifying a low number or low concentration of analytes in a sample into a detectable and repeatable (meaningful) signal.

As described above, the analyte conjugate 250 can be detected once immobilized on an electrode surface of a SPCE biosensor 100. Any suitable biosensor platform may be used, however. For example, a sample containing the analyte conjugate 250 can be applied to a capture region of a lateral flow assay device (e.g., as in U.S. Publication No. 2008/0314766, incorporated herein by reference in its entirety, with the carbohydrate moiety 156 as a capture reagent), where the capture region includes the immobilized carbohydrate moiety 156 (e.g., adsorbed onto a membrane or conjugated/bound thereto). The sample can be applied to the capture region in a variety of ways, such as by direct addition thereto or by capillary transport of the sample from an application region to the capture region. The immobilized carbohydrate moiety 156 in the capture region retains the analyte conjugate 250 in the capture region. The presence of the target analyte in the sample can be determined (e.g., and optionally quantified) by magnetically or conductimetrically detecting the analyte conjugate 250 (e.g., by detecting the magnetic nanoparticle or conductive polymer component thereof as the detection moiety) in the capture region, inasmuch as analyte probes that are not bound to target analyte are transported by capillary action out of the capture region (e.g., into an absorption region of the device).

The carbohydrate moiety 156 is capable of non-specific binding to a target analyte 230 to be detected using the biosensor 100. As contrasted with specific binding and specific binding pair members described below, the binding ability of the carbohydrate moiety 156 is not generally limited to a single type of target analyte. Such non-specific binding is generally non-covalent in nature and permits the carbohydrate moiety 156 to bind to any of a plurality of analytes in a class that encompasses the specific target analyte of interest. The non-specific binding capability the analyte 230 component of the analyte conjugate 250 permits washing of the biosensor 100 to remove excess (unbound) analyte probe 210 without (substantial) loss of the analyte conjugate 250 to be detected (FIGS. 2D and 2E).

For example, bacteria as a general class of pathogenic analytes typically include cell surface adhesin components (e.g., a surface protein or portion/sub-unit thereof, such as may be present on bacterial fimbriae) with a non-covalent, non-specific binding affinity for carbohydrate moieties. The carbohydrate moiety 156 is capable of non-specific binding to a plurality of different bacterial analytes, while a complementary analyte probe (described below) is capable of specifically binding to a selected bacterium within the plurality. Put another way, the carbohydrate moiety 156 is capable of non-specific binding to two or more species or strains within a single genus or across multiple genera, while the analyte probe is generally only capable of specific binding to a single species or strain within the class to which the carbohydrate moiety 156 can bind, or alternatively is capable of binding to fewer members of the class than the carbohydrate moiety 156. In various embodiments, the class of bacteria to which the carbohydrate moiety 156 can non-specifically bind includes multiple species or strains from bacterial genera such as *Escherichia* (e.g., *E. coli* sp., *E. coli* O157:H-sp, *E. coli* O157:H7) *Bacillus* (e.g., *B. anthracis*, Sterne strain, *B. cereus*), *Staphylococcus* (e.g., *S. aureus*), *Klebsiella* (e.g., *K. pneumonia*), *Shigella*, *Pseudomona* (e.g., *P. aerugenosa*), *Vibrio* (e.g., *V. fischeri*), and *Enterobacter*.

The carbohydrate moiety 156 can generally be a monosaccharide, a linear or branched oligosaccharide (e.g., having 2-10 saccharide residues), and/or a linear or branched polysaccharide (e.g., having more than 10 saccharide residues), including glycosides of such saccharides to provide an attachment means or chemical functional group (e.g., amine, thiol) that permits immobilization of the carbohydrate moiety 156 on the detection surface 110. Such attachment groups between the carbohydrate moiety 156 (e.g., at the non-reducing end or 1-position of the saccharide group in the carbohydrate moiety 156 to which the attachment group is linked) and the immobilization point on the detection surface suitably have 1-20 carbon atoms in an aglycone chain (e.g., in an alkyl chain, optionally including oxygen atoms in a polyether chain or chain segment in combination with an alkyl chain segment, where the chain can have a terminal functional group opposite the carbohydrate moiety 156 for immobilization). In an embodiment, the carbohydrate moiety 156 is a mannose moiety (e.g., $D_+$ mannose, such as in a mannopyranose or mannopyranoside form). The mannose moiety can be terminal (i.e., at the terminal end of a saccharide chain extending away from the detection surface 110) and/or internal in oligo- or polysaccharides. Other saccharide moieties (e.g., D or L form, such as may be naturally occurring; in a pyranose or pyranoside form) can be used alone or in combination with mannose when they can non-specifically bind to a plurality of different target analytes within a class of target analytes. A more general list of saccharide moieties that can have non-specific binding affinity to various target analytes (e.g., bacterial surface proteins) and that can be used alone (e.g., in a monosaccharide carbohydrate moiety) or in combination (e.g., in a oligo- or polysaccharide carbohydrate moiety) includes glucose (α- or β-Glu), galactose (α- or β-Gal), fucose (α- or β-Fuc), N-acetylgalactosamine (α- or β-GalNAc), N-acetylglucosamine (α- or β-GlcNAc), mannose (α- or β-Man), rhamnose (α-Rhm), N-Acetylneuraminic acid (α-Neu5Ac), glucuronic acid (β-GlcA), galacturonic acid (β-GalA), arabinofuranose acid (α-Araf), and/or xylose (α-X). In other embodiments, artificial saccharide moieties with non-specific binding affinity to given target analytes and with a resistance to natural enzymatic activity (e.g., sucralose, which has chlorine atoms providing stability to enzymatic degradation) can be used. Such saccharide moieties can improve biosensor stability insofar as natural enzymes that may be present in a sample matrix to be analyzed are less able to cleave/degrade a carbohydrate moiety immobilized on a biosensor surface.

The carbohydrate moiety 156 is suitably immobilized on the detection surface 110 via a stable covalent bond. The covalent bond is stable against degradation or further reaction (e.g., via backward equilibrium reaction kinetics resulting in bond destruction and detachment of the carbohydrate moiety 156), in particular for extended periods (e.g., at least 30, 60, 90, 180, or 360 days and/or up to 90, 180, 360, or 720 days) with or without special storage requirements (e.g., at room temperature such as 20° C.-30° C.; in a low-temperature environment such as below 20° C. (refrigerated at about 4° C., frozen, etc.); in the absence of light; in a desiccated environment). In various embodiments, the covalent bond can be between the carbohydrate moiety 156 and an intermediate immobilization means/layer 152 on the detection surface 110, or it can be directly between the carbohydrate moiety 156 and the detection surface 110.

For example, the carbohydrate moiety 156 can be immobilized by reacting a glycoside containing the carbohydrate moiety 156 and an amino group on the aglycone portion of the glycoside with an aldehyde functional group on the detection surface 110 (e.g., an aminated glycoside or aminated mannoside such as the 3-α-aminopropyl-D-mannopyranoside in Example 2). As illustrated in the examples, surface aldehyde functional groups can be provided in the form of a glutaraldehyde layer 152 applied to the detection surface 110. Reaction between the glycoside amino group and the aldehyde functional group forms an equilibrium-reversible imine bond, which can be further reduced to a stable secondary or tertiary amine covalent linking group (e.g., using cyanoborohydride).

Others methods of immobilization are possible according to techniques known in the art and depending on the particular nature of the detection surface (e.g., non-specific adsorption, specific/conjugate binding, covalent substrate attachment), such as are disclosed in U.S. Publication No. 2008/0193965, incorporated herein by reference in its entirety. For example, a thiolated glycoside containing the carbohydrate moiety 156 (e.g., 3-α-thiopropyl-D-mannopyranoside as a thiol analog to the aminoglycoside used in Example 2) for forming a covalent thiolated linkage between the carbohydrate moiety 156 and a gold or other metal surface which can be the detection surface 110 in various types of biosensors.

Analyte Probe

While the carbohydrate-functionalized biosensor 100 includes a non-specific binding carbohydrate moiety 156, methods according to the disclosure suitably include an analyte probe 210 for extraction, detection, and/or identification of a specific target analyte 230 within the class of analytes to which the carbohydrate moiety 156 can non-specifically bind (FIGS. 1A and 1B). The analyte probe 210 generally includes a specific binding pair member 214 capable of specifically binding to the specific analyte 230, and a detection moiety 212 bound to the specific binding pair member 214. The detection moiety 212 can include a separation/concentration component 212A and a detection component 212B. In an embodiment, the analyte probe 210 has a core-shell configuration in which the detection moiety 212 is in the form of a single particle having the separation/concentration component 212A as a core and the detection component 212B as a shell (FIG. 1A). In another embodiment, two analyte probes 210A, 210B in the form of separate particles are used to form the analyte conjugate 250: a probe 210A formed from a separation/concentration particle 212A having a specific binding pair member 214A and a probe 210B formed from a detection particle 212B having a specific binding pair member 214B (FIG. 1B). Contact between the analyte probe 210 (or probes 210A and 210B) and the specific analyte 230 results in a specific binding pair interaction between the two (or three) moieties to form the analyte conjugate 250 that is subsequently immobilized and detected with the carbohydrate-functionalized biosensor 100.

As described in more detail below, the specific binding pair member 214 can be an antibody (e.g., monoclonal, polyclonal) whose specific antigen is the target analyte 230.

The detection moiety 212 is not particularly limited and can include components that permit detection by various methods such as optical, conductimetric, and/or magnetic detection methods, including those described below as being suitable as detection labels. Detection of the detection moiety 212 in the analyte conjugate 250 by the biosensor 100 can be correlated to the presence of the target analyte 230 in the analyte conjugate 250 and/or the original sample used to form the analyte conjugate 250. In an embodiment, the detection moiety 212 of the probe 210/conjugate 250 can be a conductive polymer (e.g., detection shell or particle 212B) to facilitate conductimetric detection of the same. In a refinement, the conductive polymer 212B can be a component of a biologically enhanced, electrically active magnetic (BEAM) nanoparticle composition as described in detail below (e.g., a magnetic separation/concentration core 212A). In another refinement, the conductive polymer 212B can be in the form of a nanoparticle to which the specific binding pair member 214B is attached. In such case, methods for the extraction/separation of the target analyte 230 from a sample can use a separate magnetic nanoparticle capture composition that includes a magnetic nanoparticle 212A (e.g., polymeric nanoparticles such as DYNABEADS available from Invitrogen, (Carlsbad, Calif.)), and an additional specific binding pair member 214A that is bound to the magnetic nanoparticle 212A and is capable of specifically binding to the target analyte 230 (e.g., where the additional specific binding pair member 214A can be the same or different as the binding pair member 214B).

Particulate Composition

The particulate compositions according to the disclosure generally include a conductive polymer bound to magnetic nanoparticles (e.g., a population of magnetic nanoparticles in which each nanoparticle generally has at least some conductive polymer bound thereto). U.S. Publication No. 2009/0123939, the entire contents of which are hereby incorporated herein by reference, discloses particulate compositions, biologically enhanced particulate compositions and related methods suitable for use according to the present disclosure.

The conductive properties of the conductive polymer (sometimes referenced as a synthetic metal) arise from the π-electron backbone and the single/double bonds of the π-conjugated system alternating down the polymer chain. Some conducting polymeric structures include polyaniline (PANi), polypyrrole, polyacetylene, and polyphenylene. Polyaniline, in particular, has been studied thoroughly because of its stability in fluid form, conductive properties, and strong bio-molecular interactions. Conductive polymers can be used in a biosensor, an analytical device capable of pathogen detection in which the conductive polymers act as electrochemical transducers to transform biological signals to electric signals that can be detected and quantified.

The conductive polymers according to the disclosure are not particularly limited and generally include any polymer that is electrically conductive. Preferably, the conductive polymer is fluid-mobile when bound to an analyte. Suitable examples of conductive polymers are polyanilines, polypyrrole, and polythiophenes, which are dispersible in water and are conductive because of the presence of an anion or cation in the polymer (e.g., resulting from acid-doping of the polymer or monomer). Other electrically conductive polymers include substituted and unsubstituted polyanilines, polyparaphenylenes, polyparaphenylene vinylenes, polythiophenes, polypyrroles, polyfurans, polyselenophenes, polyisothianapthenes, polyphenylene sulfides, polyacetylenes, polypyridyl vinylenes, biomaterials, biopolymers, conductive carbohydrates, conductive polysaccharides, combinations thereof and blends thereof with other polymers, copolymers of the monomers thereof. Conductive polyanilines are preferred. Polyaniline is perhaps the most studied conducting polymer in a family that includes polypyrrole, polyacetylene, and polythiophene. As both electrical conductor and organic compound, polyaniline possesses flexibility, robustness, highly controllable chemical and electrical properties, simple synthesis, low cost, efficient electronic charge transfer, and environmental stability. Addition of a protic solvent such as hydrochloric acid yields a conducting form of polyaniline, with an increase in conductivity of up to ten orders of magnitude. Illustrative are the conductive polymers described in U.S. Pat. Nos. 6,333,425, 6,333,145, 6,331,356 and 6,315,926. Preferably, the conductive polymers do not contain metals in their metallic form.

The conductive polymer provides a substrate for the subsequent attachment of a binding pair member bound thereto, which binding pair member is complementary to a target analyte and thereby forms a BEAM nanoparticle, as described below. The electrically conductive characteristics of the conductive polymer also can facilitate detection of an analyte bound to the BEAM nanoparticle, for example by measuring the electrical resistance or conductance through a plurality of BEAM nanoparticles immobilized in a capture region of conductimetric biosensor device. Additionally, an electrical current passing through plurality of BEAM nanoparticles can be used to induce a magnetic field, and properties such as magnetic permeability or mass magnetization can be detected and correlated to the presence of the target analyte in a sample.

The magnetic nanoparticles according to the disclosure are not particularly limited and generally include any nano-sized particles (e.g., about 1 nm to about 1000 nm) that can be magnetized with an external magnetic/electrical field. The magnetic nanoparticles more particularly include superparamagnetic particles, which particles can be easily magnetized with an external magnetic field (e.g., to facilitate separation or concentration of the particles from the bulk of a sample medium) and then redispersed immediately once the magnet is removed (e.g., in a new (concentrated) sample medium). Thus, the magnetic nanoparticles are generally separable from solution with a conventional magnet. Suitable magnetic nanoparticles are provided as magnetic fluids or ferrofluids, and mainly include nano-sized iron oxide particles ($Fe_3O_4$ (magnetite) or $\gamma$-$Fe_2O_3$ (maghemite)) suspended in a carrier liquid. Such magnetic nanoparticles can be prepared by superparamagnetic iron oxide by precipitation of ferric and ferrous salts in the presence of sodium hydroxide and subsequent washing with water. A suitable source of $\gamma$-$Fe_2O_3$ is Sigma-Aldrich (St. Louis, Mo.), which is available as a nano-powder having particles sized at <50 nm with a specific surface area ranging from about 50 $m^2$/g to about 250 $m^2$/g. Preferably, the magnetic nanoparticles have a small size distribution (e.g., ranging from about 5 nm to about 25 nm) and uniform surface properties (e.g., about 50 $m^2$/g to about 245 $m^2$/g.).

More generally, the magnetic nanoparticles can include ferromagnetic nanoparticles (i.e., iron-containing particles providing electrical conduction or resistance). Suitable ferromagnetic nanoparticles include iron-containing magnetic metal oxides (paramagnetic or superparamagnetic), for example those including iron either as Fe(II), Fe(III), or a mixture of Fe(II)/Fe(III). Non-limiting examples of such oxides include FeO, $\gamma$-$Fe_2O_3$ (maghemite), and $Fe_3O_4$ (magnetite). The magnetic nanoparticles can also be a mixed metal oxide of the type $M1_xM2_{3-x}O_4$, wherein M1 represents a divalent metal ion and M2 represents a trivalent metal ion. For example, the magnetic nanoparticles may be magnetic ferrites of the formula $M1Fe_2O_4$, wherein M1 represents a divalent ion selected from Mn, Co, Ni, Cu, Zn, or Ba, pure or in admixture with each other or in admixture with ferrous ions. Other metal oxides include aluminium oxide, chromium oxide, copper oxide, manganese oxide, lead oxide, tin oxide, titanium oxide, zinc oxide and zirconium oxide, and suitable metals include Fe, Cr, Ni or magnetic alloys.

The particulate composition is generally formed by the polymerization of a conductive polymer monomer (e.g., aniline, pyrrole) in a solution (e.g., aqueous) containing the magnetic nanoparticles. The polymerization solution generally includes an acid dopant (e.g., HCl) to impart electrical conductivity to the resulting polymer. The polymerization reaction is preferably initiated by the addition of an oxidant (e.g., ammonium persulfate). Upon completion of the polymerization reaction, the solution contains the particulate composition in which the resulting conductive polymer is bound to the magnetic nanoparticles. The magnetic nanoparticles and the monomer can be combined in any suitable weight ratio in the polymerization solution so that the resulting particulate composition has a desired balance of magnetic, electrical, and particle size properties. For example, the weight ratio of monomer:magnetic nanoparticles in the polymerization solution (or conductive polymer: magnetic nanoparticles in the resulting particulate composition) preferably ranges from about 0.01 to about 10, more preferably from about 0.1 to about 1 or about 0.4 to about 0.8, for example about 0.6. Similarly, the particulate composition preferably ranges in size from about 1 nm to about 500 nm, more preferably about 10 nm to about 200 nm or about 50 nm to about 100 nm.

Biologically Enhanced, Electrically Active Magnetic Nanoparticles

The particulate composition in any of its above embodiments can be extended to a biologically enhanced, electrically active magnetic (BEAM) nanoparticle composition by further including a binding pair member (e.g., specific binding pair member) bound to the conductive polymer of the particulate composition. The binding pair member is selected to be complementary to a target analyte so that the BEAM nanoparticle composition can be used for the selective detection of the target analyte in a sample.

An analyte (or target analyte) generally includes a chemical or biological material, including living cells, in a sample which is to be detected using the BEAM nanoparticle composition or other analyte probe. The analyte can include pathogens of interest (e.g., bacterial pathogens such as $E.$ $coli$ O157:H7, $B.$ $anthracis$, $B.$ $cereus$, in addition to those listed above). The analyte also may be an antigen, an antibody, a ligand (i.e., an organic compound for which a receptor naturally exists or can be prepared, for example one that is mono- or polyepitopic, antigenic, or haptenic), a single compound or plurality of compounds that share at least one common epitopic site, and a receptor (i.e., a compound capable of binding to an epitopic or determinant site of a ligand, for example thyroxine binding globulin, antibodies, enzymes, Fab fragments, lectins, nucleic acids, protein A, complement component C1q). In some embodiments, the term "analyte" also can include an analog of the analyte (i.e., a modified form of the analyte which can compete with the analyte for a receptor) that can also be detected using the BEAM nanoparticle composition.

A sample generally includes an aliquot of any matter containing, or suspected of containing, the target analyte. For example, samples can include biological samples, such as samples from taken from animals (e.g., saliva, whole blood, serum, plasma, urine, tears, milk, and the like), cell cultures, plants; environmental samples (e.g., water); industrial samples; and food samples (e.g., solid or liquid foods in raw or processed form, such as milk). Samples may be required to be prepared prior to analysis according to the disclosed methods. For example, samples may require extraction, dilution, filtration, centrifugation, and/or stabilization prior to analysis. For the purposes herein, "sample" can refer to either a raw sample as originally collected or a sample resulting from one or more preparation techniques applied to the raw sample. Accordingly, a sample to be tested by contact with an analyte probe can be a liquid medium containing the analyte, where the liquid medium can be the raw sample to be tested (e.g., milk), or it can be a liquid medium (e.g., a buffer) to which a solid or liquid raw sample to be tested is added.

The specific binding pair member generally includes one of two different molecules, each having a region or area on its surface or in a cavity that specifically binds to (i.e., is complementary with) a particular spatial and polar organization of the other molecule. The binding pair members can be referenced as a ligand/receptor (or antiligand) pair. These binding pair members include members of an immunological pair such as antigen-antibody. Other specific binding pairs such as biotin-avidin (or derivatives thereof such as streptavidin or neutravidin), hormones-hormone receptors, IgG-protein A, polynucleotide pairs (e.g., DNA-DNA, DNA-RNA), DNA aptamers, and whole cells are not immunological pairs, but can be used as binding pair members within the context of the present disclosure.

Preferably, the binding pair members are specific to each other and are selected such that one binding pair member is the target analyte of interest or a component thereof (e.g., a specific surface protein or other surface component of specific bacteria or other pathogen of interest), and the other binding pair member is the constituent bound to the conductive polymer of the particulate composition. Binding specificity (or specific binding) refers to the substantial recognition of a first molecule for a second molecule (i.e., the first and second members of the binding pair), for example a polypeptide and a polyclonal or monoclonal antibody, an antibody fragment (e.g., a Fv, single chain Fv, Fab', or F(ab')$_2$ fragment) specific for the polypeptide, enzyme-substrate interactions, and polynucleotide hybridization interactions. Preferably, the binding pair members exhibit a substantial degree of binding specificity and do not exhibit a substantial amount of non-specific binding (i.e., non-covalent binding between molecules that is relatively independent of the specific structures of the molecules, for example resulting from factors including electrostatic and hydrophobic interactions between molecules).

Substantial binding specificity refers to an amount of specific binding or recognition between molecules in an assay mixture under particular assay conditions. Substantial binding specificity relates to the extent that the first and second members of the binding pair to bind only with each other and do not bind to other interfering molecules that may be present in the analytical sample. The specificity of the first and second binding pair members for each other as compared to potential interfering molecules should be sufficient to allow a meaningful assay to be conducted for the target analyte. The substantial binding specificity can be a function of a particular set of assay conditions, which includes the relative concentrations of the molecules, the time and temperature of an incubation, etc. For example, the reactivity of one binding pair member with an interfering molecule as compared to that with the second binding pair member is preferably less than about 25%, more preferably less than about 10% or about 5%.

A preferred binding pair member is an antibody (an immunoglobulin) that specifically binds to and is thereby defined as complementary with a particular spatial and polar organization of another molecule (e.g., an antigen). Antibodies generally include Y-shaped proteins on the surface of B cells that specifically bind to antigens such as bacteria, viruses, etc. The antibody can be monoclonal or polyclonal and can be prepared by techniques that are well known in the art such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies may include a complete immunoglobulin or fragment thereof, which immunoglobulins include the various classes and isotypes, such as IgA, IgD, IgE, IgG1, IgG2a, IgG2b, IgG3, IgM, etc. Fragments thereof may include Fab, Fv and F(ab')$_2$, and Fab'. In addition, aggregates, polymers, and conjugates of immunoglobulins or their fragments can be used where appropriate so long as binding affinity for a particular molecule is maintained.

The specific binding pair member that is specific to the target analyte can be bound directly or indirectly to the conductive polymer of the particulate composition (or to the detection moiety of the analyte probe more generally) by any of a variety of methods known in the art appropriate for the particular binding pair member (e.g., antibody, DNA oligonucleotide). For example, antibodies can be bound (e.g., by direct physical adsorption) to the conductive polymer of the particulate composition by incubating the antibodies in a buffer (e.g., a phosphate buffer at a pH of about 7.4 containing dimethylformamide and lithium chloride) suspension of the particulate composition. Alternatively, the particulate composition can be first incubated in the presence of a suitable linker (e.g., glutaraldehyde) followed by incubation with the antibodies to bind the antibodies thereto (e.g., glutaraldehyde can form a link between the antibodies and the particulate composition, such as the conductive polymer component thereof). Similarly, oligonucleotides can be incubated in a buffer (e.g., an acetate buffer at a pH of about 5.2) suspension of the particulate composition that also includes an immunoconjugating agent (e.g., 1-ethyl-3-(3-dimethylaminopropyl) carbodiimide hydrochloride ("EDAC")). After a suitable incubation period (i.e., depending on the rate of binding between the binding pair member and the conductive polymer) the resulting BEAM nanoparticles can be blocked, washed, centrifuged, and then stored as a suspension (e.g., in aqueous LiCl for an antibody on a phosphate-buffered saline ("PBS") solution for an oligonucleotide).

Applications of Carbohydrate-Functionalized Biosensors

As generally illustrated in FIGS. 1A-1C and 2A-2E, the biosensor 100 and the analyte probe 210 of any of the above embodiments can be used in an assay to detect the presence of a target analyte 230 in a sample 220 (e.g., which can contain a target analyte 230 of interest as well as non-target components or analytes, such as analytes within the scope of non-specific binding of the carbohydrate moiety 156). Specific detection of the target analyte 230 is effected using an analyte probe 210 (or probes 210A/210B) having a detection moiety 212 (illustrated as an EAM nanoparticle in the figures) and a specific binding pair member 214 selected to be complementary to the target analyte 230. For example, in an assay to detect *Escherichia coli* O157:H7 using BEAM nanoparticles, the analyte probe 210 can include an anti-*Escherichia coli* O157:H7 antibody bound to the conductive polymer of the particulate composition. The analyte probe 210 can be provided in a variety of forms, for example a liquid suspension, a powder, or as part of an assay device (e.g., in an application region of a lateral flow assay device).

The analyte probe 210 is contacted with the sample 220 for a time sufficient to bind any target analyte 230 in the sample 220 to the specific binding pair member 214 of the probe 210, thereby forming an analyte conjugate 250 (e.g., in which the specific binding pair member 214 links the target analyte 230 and the detection moiety 212). The sample 220 and analyte probe 210 can be contacted in any convenient way, for example by combining the two components in a reaction vessel (e.g., adding the sample 220 to a suspension of the analyte probe 210, adding the analyte probe 210 to a liquid sample 220, adding each component to a third vessel). Alternatively, when the analyte probe 210 is provided in the application region of a lateral flow assay device, the sample 220 (in liquid form) can be added to the application region of the lateral flow assay device. In another embodiment, the analyte probe 210 and the sample 220 can be pre-mixed in a vessel to form the analyte conjugate 250, magnetically separated from the remainder of the sample, and then added to the application region of a lateral flow assay device. The contact time required to obtain sufficient binding between the target analyte and the binding pair member generally depends on the kinetics of the particular analyte-binding pair member interaction. However, sufficient contact times are generally short, for example less than about 20 minutes, more preferably ranging from about 2 minutes to about 10 minutes of from about 2 minutes to about 6 minutes. Contact times can be regulated directly in a reaction vessel, while the specific construction of the lateral flow assay device (e.g., membrane size and/or material selection) can be used to regulate the contact times in such a device.

Figure 1C:
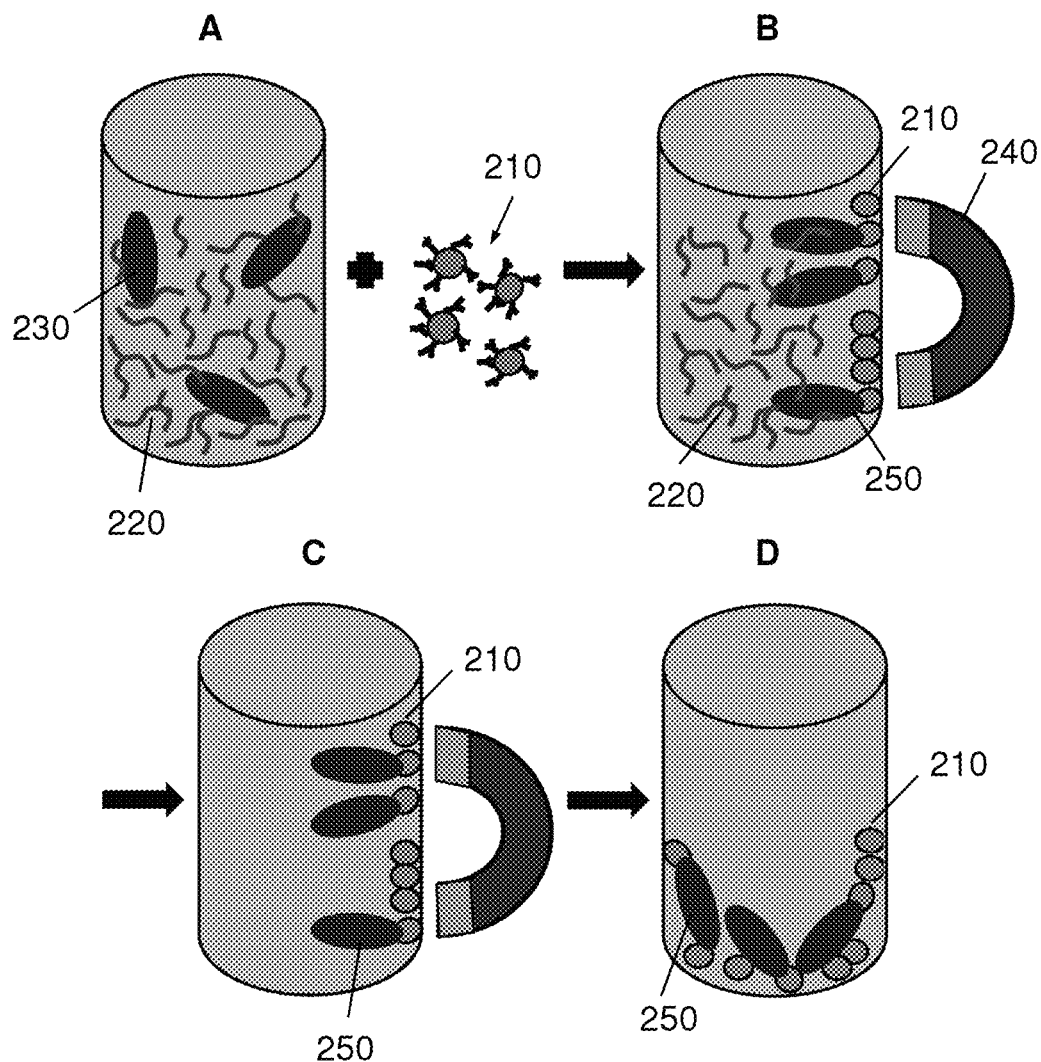
FIG. 1C illustrates an immunomagnetic separation (IMS) process according to the disclosure for the capture and separation of an *E. coli* O157:H7 analyte using a Mab-EAMNP analyte probe (panel A: sample matrix with target analyte plus Mab-EAMNPs; panel B: incubation to form an analyte-Mab-EAMNP conjugate with magnetic separation/concentration of same; panel C: magnetic concentration and washing/purification of conjugates to remove sample matrix; panel D: purified and/or concentrated analyte-Mab-EAMNP conjugate (illustrated as a bacterium such as *E. coli* O157:H7-Mab-EAMNP complex)).

In some embodiments (e.g., when the analyte probe 210 and/or the analyte conjugate 250 includes a magnetic or magnetically attractable moiety, for example as the separation/concentration component 212A of the detection moiety 212), a magnetic field (e.g., using a magnet 240) can be applied to the sample 220 to concentrate the analyte conjugate 250 using an immunomagnetic separation process. Specifically, the applied magnetic field attracts the magnetic portion of the analyte conjugate 250, causing individual particles of the analyte conjugate 250 to migrate to and concentrate in a region of the assay reaction vessel. Thus, after migration of the complex, a portion of the sample 220 that is substantially free from the analyte conjugate 250 can be removed (e.g., by draining, skimming, pipetting, etc.), thereby forming a sample concentrate that contains substantially all of the analyte conjugate 250. Preferably, at least about 80 wt. % to about 90 wt. % of the analyte conjugate 250 is recovered in the sample concentrate. Similarly, the concentration factor (i.e., the ratio of the concentration of the analyte conjugate 250 in the sample concentrate as compared to the original sample) is at least about 5, more preferably in the range of about 10 to about 50. If desired, the sample concentrate can then be removed from the assay reaction vessel (e.g., with or without an additional wash fluid) for subsequent analyte detection. As illustrated in FIG. 1C (panel C), the sample concentrate can include some free analyte probes 210' that are not conjugated to an analyte 230 (e.g., resulting from an excess of added analyte probe 210 relative to the target analyte 230 present in the sample 220).

The analyte conjugate 250 is then immobilized on the detection surface 110 of the carbohydrate-functionalized biosensor 100. Immobilization can be effected by contacting the analyte conjugate 250 with the detection surface 110 under conditions sufficient to non-specifically bind the carbohydrate moiety 156 to the target analyte 230 of the analyte conjugate 250. As above, the particular conditions can depend on the specific binding interaction, but room-temperature incubation (e.g., at 20° C. to 30° C.) for 2-60 minutes (e.g., 5-30 minutes, 10-20 minutes) before rinsing and detection is generally suitable. As illustrated in FIG. 2D for the specific case of a SPCE biosensor 100, the analyte conjugate 250 is immobilized on/over a working electrode 110 (i.e., as the detection surface 110) and adjacent a counter/reference electrode 120 of an electrochemical biosensor 100 for performing conductimetric or electrochemical detection. In this case, the analyte conjugate 250 can be applied directly to the detection surface 110 (e.g., by pipetting a liquid suspension of the analyte conjugate 250, such as that resulting from an immunomagnetic separation process). In another embodiment (not shown), the analyte conjugate can be immobilized on a detection surface and between opposing electrodes of an electrochemical biosensor device for performing conductimetric or electrochemical detection. For example, the analyte conjugate 250 can be applied to a capture region of a lateral flow assay device, where the capture region includes the carbohydrate moiety 156 (e.g., adsorbed onto a membrane). The analyte conjugate 250 can be applied to the capture region in a variety of ways, such as by direct addition thereto or by capillary transport of a liquid medium containing the analyte conjugate 250 from an application region to the capture region. Free analyte probes 210' that are not bound to target analyte 230 are transported by capillary action out of the capture region (e.g., into an absorption region of the device).

Prior to detection of the detection moiety 212 of the analyte conjugate 250, the detection surface 110 having the analyte conjugate 250 immobilized thereon is suitably washed (e.g., by rinsing with DI water or other suitable wash fluid). Washing enhances the qualitative and quantitative accuracy of the assay, because it provides a means to eliminate free analyte probes 210' on the detection surface 110 that are not bound to any target analyte 230 (but which would otherwise be detectable and contribute to a false positive or positively biased concentration due to the presence of the detection moiety 212 component). Because the free analyte probes 210' are not conjugated to any analyte 230, they are not subject to non-specific binding/immobilization interactions with the carbohydrate moiety 156 and they can be freely washed away with the rinse fluid (e.g., along with any other non-target components that may be residually present in the material applied to the detection surface 110).

Similarly prior to detecting the detection moiety 212 of the analyte conjugate 250, the detection moiety 212 is suitably electrically activated in embodiments where it includes a conductive polymer moiety. Such re-activation forms an electrically activated analyte conjugate 250 having an increased electrical conductivity relative to the analyte conjugate 250 (e.g., where the electrical conductivity of the conductive polymer as originally formed can be reduced during sample capture, extraction, and concentration steps). Suitable methods for re-activation include acid-doping the analyte conjugate 250, such as by contacting it with a strong acid (e.g., HCl, $HNO_3$, $H_2SO_4$) or a weak acid.

The biosensor 100 is then used to detect the presence of the immobilized analyte conjugate 250 via the detection moiety 212 thereof. A positive identification of the analyte conjugate 250 in the sample (concentrate) applied to the detection surface 110 indicates the presence of the target analyte 230 in the original sample 220. If a quantitative determination of the analyte conjugate 250 is made, any dilution and concentration factors can be used to determine the concentration of the target analyte 230 in the original sample 220. The specific method of detection of the analyte-nanoparticle complex is not particularly limiting, and can include methods applicable to immunoassays in general or immunomagnetic assays in particular (e.g., agglomeration, spectrophotometric detection, colorimetric detection, radioactive detection, visual inspection). In the method illustrated in the figures and examples, the detection moiety 212 includes an electrically conductive polymer that can be conductimetrically or electrochemically detected (e.g., by performing cyclic voltammetry to detect the conductive polymer moiety of the electrically activated analyte conjugate 250, such as detection of impedance due to captured target analyte cells balanced with the conductance of the conductive polymer moiety in the analyte conjugate and using a blank reference from unbound analyte probes to evaluate a change in conductivity).

In other embodiments, the analyte conjugate 250 in the sample (concentrate) is detected by (1) contacting the sample with a detection label for a time sufficient to bind the detection label to the analyte conjugate 250, thereby forming a label-analyte conjugate, wherein either (i) the detection label is complementary to the target analyte and the detection label binds to the target analyte bound to the analyte conjugate 250 or (ii) the detection label is complementary to the binding pair member and the detection label binds to a free binding pair member of the analyte conjugate 250, (2) removing any free detection label that is not bound in the label-analyte conjugate from the sample (e.g., by washing), and (3) detecting the detection label remaining in the sample concentrate that is bound in the label-analyte conjugate as part of the detection moiety.

The detection label is generally part of a conjugate reagent that includes a label and an analyte-specific binding partner (in which case the detection label binds to the target analyte of the analyte-nanoparticle complex) or an analyte analog (in which case the detection label binds to free binding pair members of the analyte-nanoparticle complex). In an alternate embodiment, the detection label can be directly bound to the conductive polymer of the particulate composition. Such an embodiment can be useful, for example, when the labeled BEAM nanoparticles are used in a capture assay in which the labeled BEAM nanoparticles that are conjugated with the target analyte are immobilized in a capture region of a detection device such that the detection label can then facilitate detection of the target analyte in the capture region.

A label can include any molecule that is bound (via covalent or non-covalent means, alone or encapsulated) to another molecule or solid support and that is chosen for specific characteristics that allow detection of the labeled molecule. Generally, labels can include enzymes, chromogenic substrates, chromophores, radioisotopes, fluorescent molecules, chemiluminescent molecules, phosphorescent molecules, direct visual labels, and combinations thereof. Thus, the detection label can include labeled binding pair members that are complementary to the target analyte, for example including enzyme-, radioisotope-, and fluorescent ion-labeled antibodies. The utilization of a label produces a signal that may be detected by means such as detection of electromagnetic radiation, direct visualization, spectrophotometry, etc., which signal also can optionally be measured and/or quantitated. When the detection label binds to the target analyte (or to the conductive polymer directly in a capture assay), the measured signal is proportional to the amount of the analyte in the original sample; conversely, when the detection label includes an analyte analog that binds to the free binding pair members, the measured signal is inversely proportional to the amount of the analyte in the original sample.

Figure 3:
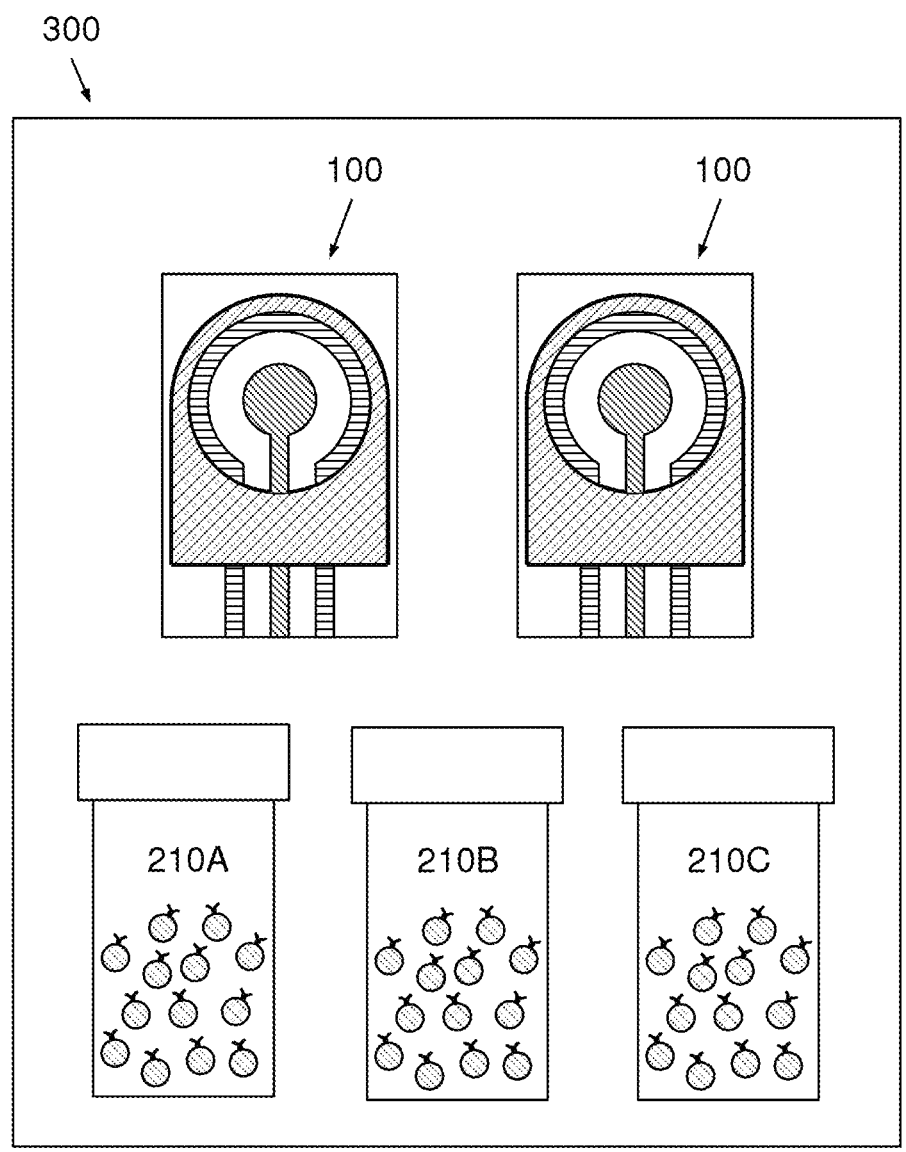
FIG. 3 illustrates a kit including one or more (different) functionalized biosensors and one or more (different) analyte probes according to the disclosure.

The disclosed compositions also can be provided in a kit 300 (FIG. 3). A suitable kit 300 includes an analyte probe 210 specific to a desired analyte 230 as well as carbohydrate-functionalized biosensor 100 with a carbohydrate moiety 156 capable of non-specific binding to the target analyte 230. In an embodiment, the kit 300 can be intended for multiplexed analysis of several different target analytes 230 such that it contains a plurality of different analyte probes 210, where each analyte probe 210 has a specific binding pair member 214 capable of specifically binding to a different target analyte 230 (e.g., probes 210A, 210B, and 210C specific to different analytes as illustrated in FIG. 3). In such case, the kit 300 can include one or a plurality of carbohydrate-functionalized biosensors 100, in particular where each biosensor has the same carbohydrate moiety 156, but is nonetheless capable of non-specific binding to all of the separately targeted analytes 230 by the different probes 210. The kit 300 can generally include a variety of other optional components that may be desired and/or appropriate, for example a reaction vessel (e.g., a container for mixing the analyte probe 210 and a sample 220 to be analyzed), a magnet, wash reagents, detector reagents (i.e., which cause the detection label to provide its detectable signal), positive and/or negative control reagents, assay kit instructions according to any of the methods disclosed herein, and other additives (e.g., stabilizers, buffers). The relative amounts of the various reagents may be varied widely, to provide for concentrations in solution of the reagents that substantially optimize the sensitivity of the assay. Particularly, the reagents may be provided as dry powders (e.g., lyophilized) which on dissolution will provide for a reagent solution having the appropriate concentrations for combining with the sample 220.

EXAMPLES

The following examples illustrate the disclosed compositions and methods, but are not intended to limit the scope of any claims thereto.

Specific binding pair members (e.g., antibodies such as polyclonal antibodies Pab specific to the analyte) immobilized on a biosensor surface can bind to the target organism in a second site from an already bound BEAM-analyte complex (e.g., including a monoclonal antibody Mab specific to the analyte) and holds it to the biosensor surface (e.g., a screen-printed carbon electrode (SPCE) surface). This allows rinsing of BEAM nanoparticles that are not bound to a target analyte and permits a more direct correlation of the amount of conductive polymer (e.g., polyaniline in a BEAM nanoparticle composition) with the corresponding amount of analyte (e.g., bacteria) in the BEAM-analyte complex and, accordingly, also in the original sample. Unfortunately, Pab-functionalized screen printed carbon electrodes (Pab-SPCEs) have limited shelf stability, requiring controlled storage at 4° C. They also degrade rather quickly, insofar as conjugation methods used to immobilize the Pab on the biosensor surface are generally reversible at room temperature. Further, the Pab-SPCEs are specific to one bacterial species, preventing multiplexing of the system to detect multiple different analyte targets using a single type of functionalized SPCE.

The examples specifically examine the use of an immobilized carbohydrate moiety on a biosensor surface as a non-specific binding pair member to capture and itself immobilize a BEAM-analyte complex for subsequent detection with the biosensor. The examples illustrate the use of a $D_+$ mannose saccharide as a carbohydrate moiety that is capable of non-specific binding to a variety of different target organism analytes. $D_+$ mannose is a sugar (stable in the environment) for which organisms such as E. coli O157:H7, V. cholera, and the Enterobacteriacea genus have an affinity for in vivo cell entry. Carbohydrates are more stable than a Pab or a protein and allow multiple bacteria to non-specifically bind thereto, thereby also allowing multiplexed detection of different analytes using (e.g., where specific analyte binding and detection is provided by the specific binding pair member on the BEAM nanoparticles). Multiplexing allows easier, faster sample evaluation in the field of real sample matrices. In the following examples, an aminated $D_+$ mannose saccharide is immobilized on an SPCE biosensor using a glutaraldehyde linker followed by reduction to form stable covalent bonds (i.e., those not subject to reversible equilibrium kinetics), thus providing a shelf-stable biosensor platform. The examples further evaluate the inclusivity of the carbohydrate-functionalized SPCE, its limits of detection in broth and whole liquid milk samples, and its sensitivity and specificity in whole liquid milk samples.

Materials and Methods: Ferric chloride hexahydrate (EMD Chemicals), sodium acetate (CCI Chemicals), sodium acrylate, sodium chloride (NaCl), ethylene glycol, ethylenediamine, hydrochloric acid, aniline, iron (III) oxide nanopowder, ammonium persulfate, methanol, and diethyl ether were used as received in the synthesis of the magnetic nanoparticles. Nanoparticles were immunofunctionalized with monoclonal anti-E. coli O157:H7 antibodies obtained from Meridian Life Science, Inc. (Saco, Me.).

Polysorbate-20 (TWEEN-20), Triton X-100, phosphate buffered saline (PBS), trizma base, casein, and sodium phosphate (dibasic and monobasic) were used in the immunomagnetic separation (IMS procedure). The above reagents, unless otherwise noted, were purchased from Sigma-Aldrich (St. Louis, Mo.).

All solutions and buffers used in these examples were prepared in de-ionized (DI) water (from Millipore Direct-Q system) as follows: PBS buffer (10 mM PBS, pH 7.4), wash buffer (10 mM PBS, pH 7.4, with 0.05% Tween-20 or 0.05% Triton-X100), phosphate buffer (100 mM sodium phosphate, pH 7.4), blocking buffer (100 mM Tris-HCl buffer, pH 7.6, with 0.01% w/v casein).

All chemicals used in the synthesis of the aminated $D_+$ mannose were purchased from Sigma Aldrich (St. Louis, Mo.) unless otherwise noted. Chemicals used to functionalize the SPCE include 2.5 mM glutaraldehyde solution, citrate gold nanoparticles (AuNPs), stock≈2.4 Au; ≈15 nm in diameter, $D_+$ mannose-amine @ 25 µg/ml, and deactivating buffer (0.2 M Tris in 0.01 M PBS plus 10 mM Cyanoborohydride). Chemicals such as 0.1 M HCl solution, Acridine orange stain (2 mg of AO into 1 ml of Buffer=100×); acridine orange buffer pH 3.8 (90 ml of 10 mM (0.01 M) Phosphate Buffer, 585 mg of NaCl, qs to 100 ml), Coupling Buffer, pH 7.4 (0.1 M phosphate buffer into 900 ml of dH2O) are used as described herein.

Magnetic separations were performed with a commercial magnetic separator (Promega Corporation, Madison, Wis.). Hybridization of biological materials was carried out at room temperature with rotation on a tube rotisserie (Labquake, Thermo Scientific, MA). Scanning electron micrographs were acquired using field-emission scanning electron microscopy (JOEL 7500F, acceleration voltage of 5 kV). A superconducting quantum interference device magnetometer (Quantum design MPMS SQUID) was used for magnetic characterization of EAMNPs. SPCEs were purchased from Gwent Electronics Materials Ltd, United Kingdom and functionalized as described below. Cyclic voltammetry was performed on the PALMSENS handheld potentiostat (Palm Instruments BV, Houten The Netherlands).

E. coli O157:H7 strains, E. coli non-H7 strains, and non-E. coli bacterial strains were obtained from the Food Safety and Toxicology collection at Michigan State University (MSU). Some were from the Nano-Biosensors Laboratory at MSU culture collection and others were obtained from Neogen Inc. (Lansing, Mich.) and the University of Georgia. From frozen purified culture stocks (stored at −80° C.), colonies were isolated by streak-plate method on trypticase soy agar (BD Biosciences, MD) plates. A single colony was used to inoculate a vial of tryptic soy broth (BD Biosciences, MD) and grown overnight at 37° C. A 1 ml aliquot of the liquid culture was transferred to a new vial of broth and stored at 37° C. for up to 6 days. This culture was used to inoculate a new vial of broth with 1 ml of inoculum 10 to 24 h before each experiment to produce fresh bacterial cells which were serially diluted in 0.1% (w/v) peptone water (Fluka-Biochemika, Switzerland) prior to their use in the IMS procedure. Viable cells were enumerated by microbial plating on MacConkey agar with sorbitol (SMAC) (BD Biosciences, MD or Neogen Inc., MI), according to standard rules for plate counting (FDA, 2009). OD 600 spectrophotometer readings (BIO-RAD Smartspec 3000, Hercules, Calif.) were taken from each culture before use as compared to Trypticase Soy Broth. Three readings were taken and averaged together.

Cyclic Voltammetry:

Cyclic voltammetry is an electrochemical method where a potential is scanned from −1.4V to 2 V and the resultant current is measured. Varying parameters can be used on the resultant cyclic voltammogram, depending on the reporter used. In this case, the polyaniline shell of the BEAM nanoparticles is electrically active and can provide a peak at a certain voltage in both the positive and negative sweep of the current in the cycle if present. Larger levels of polyaniline can provide greater peak heights. Other components of the system can affect the polyaniline peak greatly. Due to this, other parameters such as delta Q (i.e., the integral of current as a function of time), peak shift, peak shape, resistance at each point in the cycle, and average resistance over the whole cycle were tabulated and evaluated. Between the differing concentrations and the blank D-SPCE, all the parameters collected were compared. The XY values of the highest, lowest and expected polyaniline peaks were evaluated from the voltammogram. The shift positive or negative from the original position of the expected peak in a polyaniline-coated D-SPCE without bacterial cells was evaluated and recorded for each run. The shapes of the characteristic peaks were also evaluated based on their width and tracing. From the collected data of voltage (V) versus current (I) at each point on the voltammogram as well as the total number of XY points (n) in the voltammogran, the absolute resistance (R) and the average resistance ($<R>$) were calculated from Equations 1 and 2, below, respectively.

$$R=|V/I| \quad \text{[Equation 1]}$$

$$<R>=(\Sigma R)/n=(\Sigma|V/I|)/n \quad \text{[Equation 2]}$$

Four scans of each D-SPCE were conducted. The first scan was discarded as a system equilibration set. The last three provided at least 960 data points apiece across the cycle. For each of these 960 individual points the absolute resistance was calculated. The average resistances of the scans were averaged together to get the single average resistance across the system for each run at each concentration of bacteria.

Example 1

Synthesis of a BEAM Composition

Synthesis of EAM Nanoparticles:

The polyaniline-coated magnetic nanoparticles (EAM nanoparticles or EAMNPs) were synthesized by polymerization and acid doping of aniline monomer around gamma iron (III) oxide ($\gamma$-$Fe_2O_3$) nanoparticles, using a slightly modified published procedure (Pal et al., 2008). Briefly, 0.650 g of iron (III) oxide nanopowder were dispersed in 50 ml of 1 M HCl, 10 ml of deionized water and 0.4 ml of aniline monomer by sonication in an ice bath for 1 h. A volume of 20 ml of 0.2 M ammonium persulfate (as oxidant) was added drop-wise to the above solution under continuous magnetic stirring. Color change from rust brown to dark green indicated formation of electrically-active (green) polyaniline over the smaller (brown) $\gamma$-$Fe_2O_3$ nanoparticles. The solution was stirred for 2 h in an ice bath and was filtered through a qualitative grade filter (2.5 µm pore size, Ahlstrom, grade 601). The supernatant thus obtained was successively filtered through a nitrocellulose membrane filter (1.2 µm pore size, Millipore) followed by washings with 10 ml each of 1 M HCl, 10% (v/v) methanol, and diethyl ether. The particles were dried overnight at room temperature under vacuum. The particles ranged in size from 1.2 to 2.5 µm, and displayed a room temperature saturation magnetization of 30 emu/g.

Formation of BEAM Nanoparticles:

The EAMNPs were conjugated with monoclonal antibodies at an initial EAMNP concentration of 10 mg/ml (1% solid). Two different initial concentrations of monoclonal antibody were used during conjugation: 1.0 mg/ml and 0.5 mg/ml. Conjugation of antibodies onto EAMNPs was performed both with and without the addition of NaCl. Conjugation of antibodies onto EAMNPs was by direct physical adsorption and electrostatic interactions. A volume of 100 µl of monoclonal anti-*E. coli* O157:H7 antibody (Mab; suspended in 0.1M phosphate buffer) was added, yielding a final antibody concentration of either 1.0 mg/ml or 0.5 mg/ml. The mixture was hybridized on a rotisserie-style rotator for 1 hour at room temperature, with 25 µl of 10×PBS being added after the first 5 min of hybridization, to increase the NaCl content of the suspension to approximately 0.14M. (For certain experiments, the 10×PBS was omitted). Following hybridization, the EAMNP-antibody conjugate (or BEAM nanoparticle) was magnetically separated, the supernatant removed, and the conjugate re-suspended in 250 µl of blocking buffer (0.1M tris buffer with 0.01% casein) for 5 min. Again the conjugate was magnetically separated, the supernatant removed, and the conjugate re-suspended in 250 µl of blocking buffer, this time for 1 hour with rotation. Finally, the EAMNP-antibody conjugate was magnetically separated, the supernatant removed, and the conjugate re-suspended in 2.5 ml of 0.1M phosphate buffered saline (PBS).

The final concentration of EAMNPs in each solution was 1.0 mg/ml. Immuno-conjugated EAMNPs (Mab-EAMNPs or BEAM nanoparticles) were stored at 4° C. Prior to experimental use, Mab-EAMNPs were either magnetically separated and concentrated or further diluted in 0.1M PBS, in order to obtain solutions of Mab-EAMNPs at the following concentrations: 1.5 mg/ml, 1.0 mg/ml, 0.5 mg/ml, and 0.1 mg/ml EAMNPs.

Immunomagnetic Separation (IMS) Using BEAM Nanoparticles:

A desired concentration of Mab-EAMNPs was added to a liquid sample matrix (e.g., broth, milk, or otherwise) potentially containing an analyte of interest (e.g., *E. coli* O157:H7 or other bacterial analyte). The mixture was hybridized with rotation at room temperature for 30 minutes to form an analyte-Mab-EAMNP conjugate for any analyte present in the liquid sample matrix. After hybridization, the analyte-Mab-EAMNP complexes were magnetically separated and the supernatant removed (e.g., by magnetic immobilization of the complexes). Complexes were washed twice in wash buffer (0.01M PBS containing 0.05% Triton-X100), and finally re-suspended in 0.5 ml of 0.01M PBS. The IMS procedure required 40 min, and is depicted in FIG. 1C.

Example 2

Fabrication of Carbohydrate-Functionalized Biosensor

Synthesis of Aminated Carbohydrate:

Aminated $D_+$ mannose (3-α-aminopropyl-D-mannopyranoside) was synthesized according to published protocols. (EI-Boubbou, *JACS*, vol. 129, p. 13392-13393, (2007)). The structure of the aminated $D_+$ mannose is shown below in Structure 1.

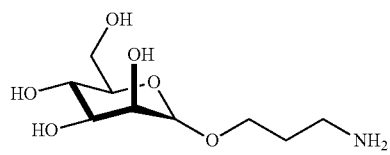

[Structure 1]

Immobilization of Aminated Carbohydrate:

To attach the aminated $D_+$ mannose to an SPCE biosensor, rinsed and dried SPCE chips were incubated with 25 μl of 2.5 mM glutaraldehyde on the working carbon electrode of the SPCE for two hours at 4° C. At completion, the excess glutaraldehyde was rinsed with DI water and dried. Citrate gold nanoparticles (AuNPs) (25 μl) were then incubated on the working carbon electrode for two hours at 4° C. At completion, the excess citrate AuNPs were rinsed with DI water and dried. On the working carbon electrode, 25 μl of aminated $D_+$ mannose (25 μg/ml) was placed for 15 minutes at 21° C. At completion, the excess aminated $D_+$ mannose was rinsed with DI water and dried and 50 μl of deactivating buffer was applied for 15 minutes at 21° C. As described above, the deactivating buffer included (i) tris(hydroxymethyl)aminomethane to block remaining active glutaraldehyde active sites (i.e., by formation of imine bonds between the tris amino group and the glutaraldehyde aldehyde group) and (ii) cyanoborohydride to convert/reduce equilibrium-reversible imine bonds (i.e., bonds that form and break in equilibrium between the glutaraldehyde and the amino groups of the aminated $D_+$ mannose and the tris blocking agent) into stable covalent amine linkages between the glutaraldehyde and the amino-containing compounds. The resultant biosensor containing irreversibly bound $D_+$ mannose moieties immobilized thereon (D-SPCE) was dried and stored at room temperature (protected from light). The formation of a stable covalent bond immobilizing the saccharide moiety on the biosensor surface improves the field stability of the functionalized SPCE biosensor, allowing the biosensor to be stored are room temperature over extended periods without substantial reduction in the non-specific binding ability of the saccharide moiety.

FIGS. 2A-2E illustrate a carbohydrate-functionalized biosensor 100 according the disclosure. The biosensor 100 is illustrated as an SPCE having a bottom surface 130 on top of which is mounted a carbon working electrode 110 and a counter/reference electrode (Ag/AgCl) 120. The working electrode 110 has a functional surface 150 thereon that includes a glutaraldehyde layer 152 having immobilized AuNPs 154 and saccharide moieties 156 (e.g., the aminated $D_+$ mannose as in the examples). In use and as described below, conjugates of BEAM nanoparticles 210 and target analytes 230 are bound to the biosensor 100 via non-specific binding interactions between the analytes 230 and the saccharide moieties 156. The biosensor 100 can include a magnet 140 (e.g., electromagnet that can be powered on and off) mounted below the bottom surface 130, which magnet 140 can be used to attract the magnetic portion of the BEAM nanoparticles 210 toward the electrode surfaces 110, 120, thereby enhancing the electrical sensitivity of the biosensor 100 (e.g., due to the closer proximity of the electrically conductive portion of the BEAM nanoparticles 210).

Example 3

Binding Activity of Carbohydrate Moiety and BEAM-Analyte Conjugates

Example 3 examined the ability of the aminated $D_+$ mannose saccharide moiety to remain biologically active when bound to the SPCE and against bacteria alone and those that are bound to the Mab-EAMNP complex. In Example 3, *E. coli* O157:H7 Sakai strain cultures were prepared as above and stained with acridine orange. Using a micropipette, 100 μl of the stained organisms were spread on SPCEs either plain, with blocked or unblocked glutaraldehyde (i.e., but without aminated $D_+$ mannose), and with blocked aminated $D_+$ mannose (i.e., as formed in Example 2). These SPCEs were incubated for 15 minutes and rinsed two times with DI water. The resultant SPCEs were evaluated under a blue filtered light microscope and then punched out and placed in a 96 well plate and evaluated with differing filter methods in the spectrophotometer. Acridine orange was also applied to an SPCE without cells or blocking. Fluorescent analysis as well as visual inspection of the stained bacteria confirmed that the D-SPCE including the blocked aminated $D_+$ mannose retain much more bacteria on the biosensor surface as compared to the other control SPCEs.

To determine whether the active binding site between $D_+$ mannose and the target analyte remained active when the Mab was attached to the target analyte, *E. coli* O157:H7 Sakai strain captured by Mab-EAMNPs were also challenged in solution with aminated $D_+$ mannose and their active conjugation to the compound evaluated using $D_+$ mannose's binding lectin (Con A) conjugated to fluorescein isothiocyanate (Con A-FITC) in the spectrophotometer. For the spectrophotometer, relative fluorescence units (RFUs) were calculated using a blank D-SPCE as the reference value of 1 RFU. Commercially prepared Con A-FITC was obtained and mixed 1:1 with aminated $D_+$ mannose in solution. That 1:1 solution was incubated 1:1 again with the same size sample of *E. coli* O157:H7 Sakai strain-Mab-EAMNP conjugate formed as described above. Con A FITC; $D_+$ mannose Con A FITC and $D_+$ mannose Con A FITC with Mab-EAMNP-captured *E. coli* O157:H7 Sakai strain were evaluated in the spectrophotometer. The Mab-EAMNP-captured *E. coli* O157:H7 Sakai was strain magnetized out, washed and re-suspended in solution before placing in the spectrophotometer. The supernatant of that rinse was also evaluated to ascertain the decrease of RFU that would have moved with the magnetized Mab-EAMNP complex. Fluorescent analysis confirmed that the active binding sites on the E. coli O157:H7 for the mannose saccharide moiety are still active when the bacterial cells are conjugated to the Mab of the EAMNP-Mab.

Example 4

Non-Specific Binding Activity of Carbohydrate-Functionalized Biosensor

Figure 4:
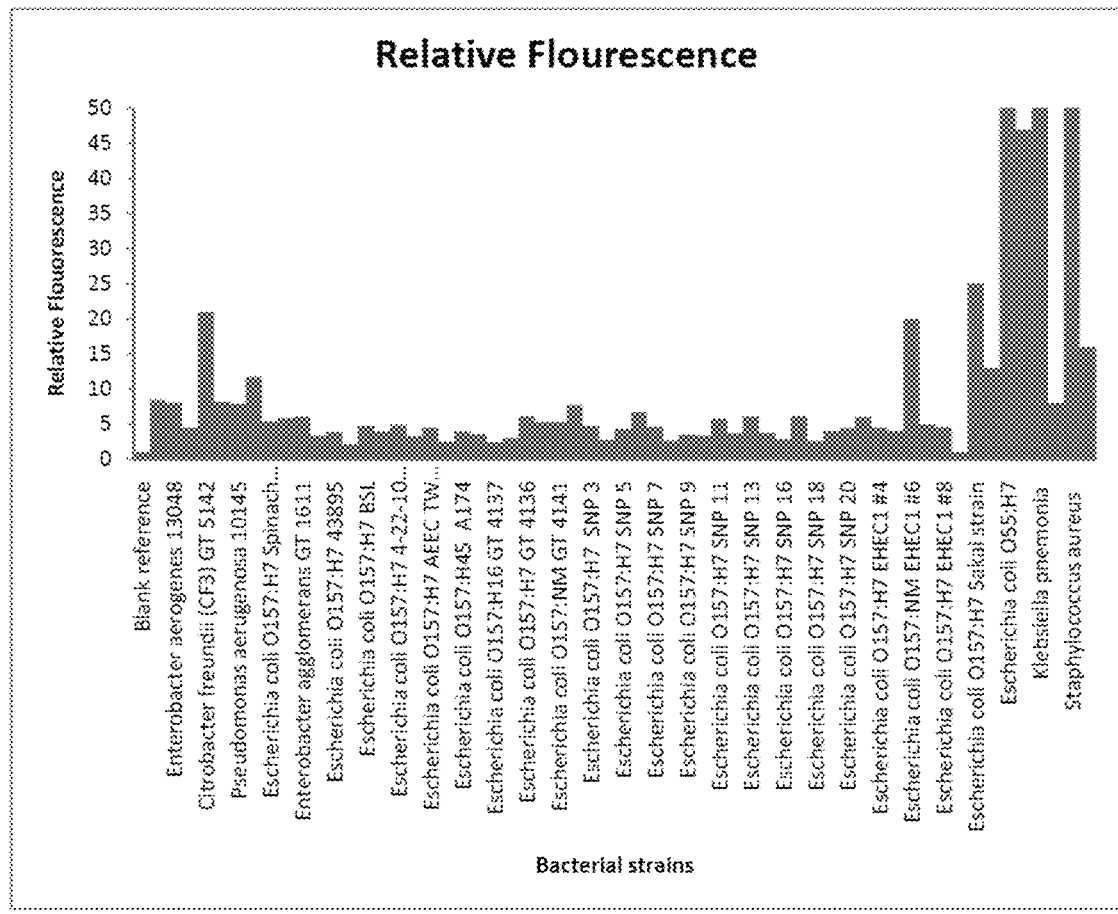
FIG. 4 is a graph illustrating the non-specific binding ability of the carbohydrate binding moiety as a function of bacterial target analyte (fluorescent intensity of captured, stained bacterial organisms compared to a blank reference).

Example 4 examined the ability of the aminated $D_+$ mannose saccharide moiety to be used as a universal detection platform for the immobilization of multiple different bacteria (e.g., different strains, species, genera, etc.). D-SPCEs as formed in Example 2 were incubated with various fluorescently stained bacterial cells (i.e., as in Example 3 but with different types of bacteria) from different families and visualized under a light microscope with an appropriate filter for the varying stains, the spectrophotometer for relative fluorescence, the confocal microscope, or the scanning electron microscope (SEM). 29 different organisms were challenged on the D-SPCE, including multiple strains of E. coli O157:H-sp., Bacillus anthracis Sterne strain, Staphalococcus aureus, Klebsiella pneumonia, E. coli sp., Shigella sp., Pseudomona aerugenosa, Vibrio fischeri, and Enterobacter sp. FIG. 4 illustrates the resultant RFUs measured for each bacteria type. Although cell concentrations were not accounted for in the data shown in FIG. 4, all bacteria challenged nonetheless attached to D-SPCEs and had RFUs much larger than blank D-SPCEs.

Example 5

Detection of E. Coli O157:H7 in Broth Sample Matrix

Example 5 examined the ability of the aminated $D_+$ mannose saccharide moiety to be used as a biosensor platform for the immobilization and detection of target analytes in a broth sample. Specifically, 100 µl of E. coli O157:H7 Sakai strain-Mab-EAMNP conjugates from broth trial samples were placed on the D-SPCE as formed in Example 2, incubated for 15 minutes and rinsed twice with DI water. They were allowed to dry, doped with 100 µl of 0.1 M HCl and evaluated, using cyclic voltammetry, on the potentiostat.

Figure 5:
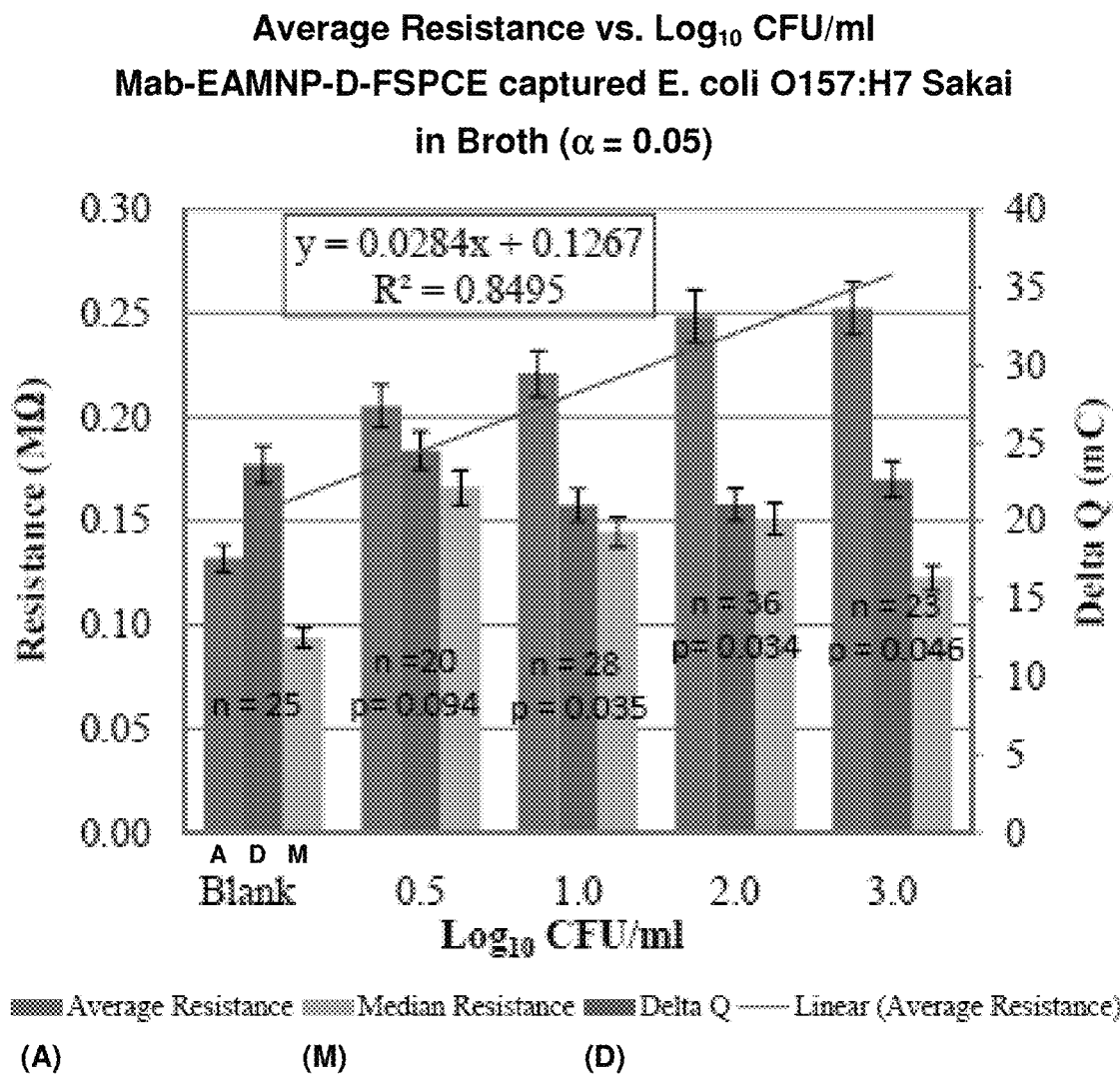
FIG. 5 is a graph illustrating the quantitative evaluation of captured *E. coli* O157:H7-Mab-EAMNP complexes in broth on a functionalized D-SPCE biosensor as a function of concentration ($Log_{10}$CFU/ml=0.5 contains 1-9.99 CFU/ml).

Several dilutions of Mab-EAMNP captured E. coli O157:H7 Sakai strains were placed on the potentiostat for cyclic voltammetry evaluation. Multiple calculations were evaluated to determine the best parameter for comparison of the concentrations and to use that parameter to determine if the biosensor is a quantitative or a qualitative test. One parameter in the initial runs showed promise to be most consistently discerning from the blank: the calculation of average resistance across the whole voltammogram. Even though the bacterial cells are attached to the $D_+$ mannose, the addition of the magnet 140 (FIG. 2B) to the underside of the SPCE improves the conductance of the system to allow clearer differences between concentrations of bacteria. FIG. 5 and Table 1 below are the broth based runs from the Mab-EAMNP IMS extraction run on the potentiostat using cyclic voltammetry, including average, delta Q, and median resistance measured quantities.

TABLE 1

Average resistance using cyclic voltammetry on Mab-EAMNP-D-FSPCE captured E. coli O157:H7 Sakai, in broth ($Log_{10}$CFU/ml contains 1-9.99 CFU/ml; cut point for a positive biosensor test was chosen at 0.14 mΩ to be used in the food trials).

| $Log_{10}$(CFU/ml) | RESISTANCE | | | Blank vs [ ] t-test | n | STDdev |
| --- | --- | --- | --- | --- | --- | --- |
| | Average | Delta Q | Median | | | |
| Blank | 0.13 | 23.62 | 0.09 | | 25 | 0.11 |
| 0.50 | 0.21 | 24.53 | 0.17 | p = 0.094 | 20 | 0.22 |
| 1.00 | 0.22 | 21.02 | 0.14 | p = 0.035 | 28 | 0.23 |
| 2.00 | 0.25 | 21.05 | 0.15 | p = 0.034 | 36 | 0.35 |
| 3.00 | 0.25 | 22.68 | 0.12 | p = 0.046 | 23 | 0.31 |
| 4.00 | 0.23 | 21.80 | 0.15 | p = 0.043 | 20 | 0.23 |
| 5.00 | 0.18 | 21.40 | 0.17 | p = 0.089 | 21 | 0.11 |
| 6.00 | 0.18 | 21.38 | 0.13 | p = 0.112 | 18 | 0.14 |
| 7.00 | 0.20 | 20.14 | 0.16 | p = 0.040 | 22 | 0.14 |
| | | | | α = 0.05 | 188 | |

Example 6

Detection of E. Coli O157:H7 in Milk Sample Matrix

Example 6 examined the ability of the aminated $D_+$ mannose saccharide moiety to be used as a biosensor platform for the immobilization and detection of 1-10 CFU/ml of E. coli O157:H7 in 200 ml whole fluid milk samples without a pre-enrichment after a selective Mab-EAMNP extraction and concentration procedure. Specifically, 100 µl of E. coli O157:H7 Sakai strain-Mab-EAMNP conjugates from milk trial samples were placed on the D-SPCE as formed in Example 2, incubated for 15 minutes, and rinsed twice with DI water. They were allowed to dry, doped with 100 µl of 0.1 M HCl and evaluated, using cyclic voltammetry, on the potentiostat. The same parameters as the broth trials (Example 5) were used as for the fluid whole milk trials for biosensor evaluation and the statistical comparisons. In addition, the data from the broth trials were used to determine a cut point other than the blank parameters to determine whether an analyzed fluid whole milk sample would be classified as being positive or negative for the presence of the E. coli O157:H7 bacteria at the tested concentration (e.g., as shown in Table 1, 0.14 mΩ for the average resistance above which the test would classified as positive).

Figure 6:
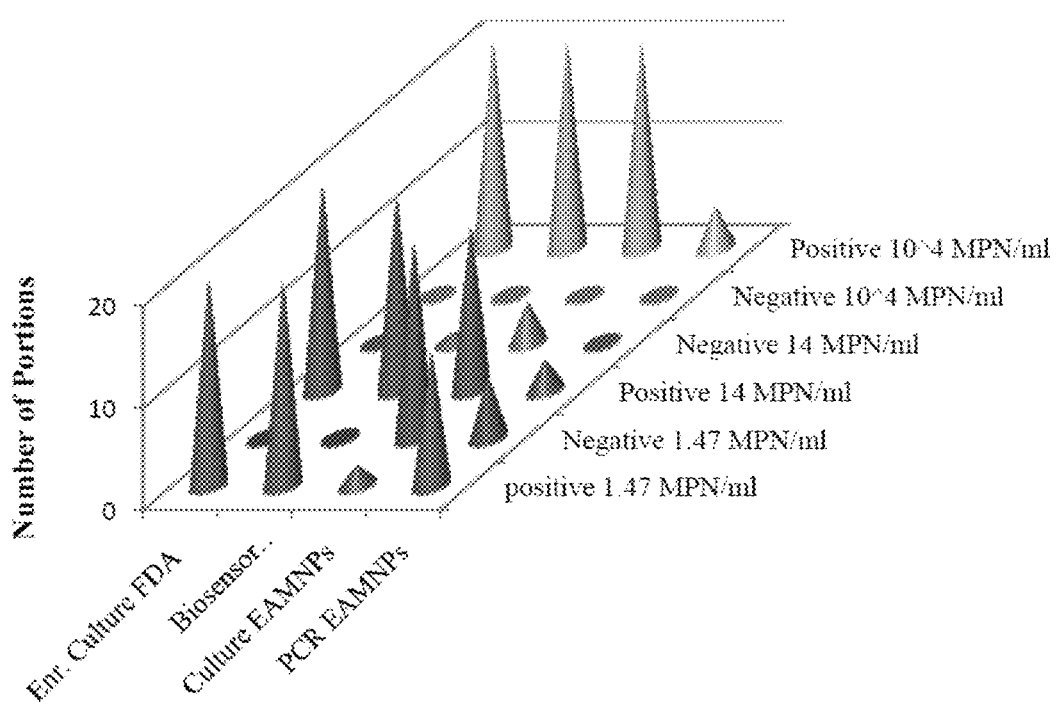
FIG. 6 is a graph illustrating the detection capability of the disclosed method for whole milk fluid samples spiked with *E. coli* O157:H7 at three different concentrations.

Spiked bulk tank milk at varying concentrations (1.47, 14, and $10^4$ MPN/ml) were evaluated (a) in 20 portions using the FDA BAM enrichment comparative method and (b) in 20 portions without enrichment using IMS separation with Mab-EAMNPs to form the analyte conjugates. The IMS-separated samples were further split and (i) cultured, (ii)

applied to and scanned by cyclic voltammetry using the carbohydrate-functionalized biosensor, and (iii) evaluated via PCR. The biosensor outperformed culture and PCR and correctly identified 20 of the 20 portions at all concentrations, as shown in FIG. 6.

The purpose of using 20-portion samples is to evaluate them as a unit. There is not enough data collected in any one concentration to determine sensitivity and specificity at each concentration, so the data was presented using the portions as separate units. When treated as a unit and 5-15 of the 20 are considered a positive diagnosis, the biosensor was correct for all three of the runs, as verified by the FDA gold standard and by the PCR. This gives a 100% sensitivity and 100% specificity. Thus, capture, extraction and detection of E. coli O157:H7 is possible for samples at concentrations less than 2 CFU/ml using EAMNPs, IMS, and D-SPCE cyclic voltammetry evaluations and average resistance across the cycle as the parameter of interest. The resistance going up from the blank in the presence of cells may mean that the conductance of the polyaniline is overridden by the impedance of the current by the cells present. Only one run at the level of 1.47 MPN/ml was performed, but this biosensor system was able to correctly identify 20 of the 20 portions at that level, whereas the culture could only identify 2 of those portions. Thus, the science-based decision to place the food on hold after a biosensor-positive result can be made in 2.5 hours with PCR confirmation. Culture on the IMS-separated portion can be completed in 24 hours if infectivity is a concern instead of just contamination. Current regulatory diagnosis is 36 hours.

Summary:

The $D_+$ mannose saccharide moiety with the amine group has successfully been attached to the SPCE and remains biologically active even to Mab-EAMNP-captured E. coli O157:H7. This indicates the active site of the Mab and the active site of the $D_+$ mannose do not overlap for this bacteria and this antibody. Multiple bacterial types are reactive with $D_+$ mannose even when functionalized to the surface of the SPCE. Statistically significant differentiation can be performed in broth by concentrations down to 10 CFU/ml in broth and milk with no pre-enrichment. Even stronger statistical significance can be obtained when the biosensor is treated like a qualitative analysis.

Many microorganisms use $D_+$ mannose as an attachment site in vivo, and the data show excellent capture of a very diverse set of organisms, which permits multiplexing (e.g., in a system including a plurality of functionalized biosensors including a mannose or other non-specific capture moiety, such that assay specificity permitting identification of a particular target analyte such as a specific bacteria is provided by a specific binding pair member on BEAM nanoparticle or other type of capture substrate). The excellent capture of the $D_+$ mannose when attached to the SPCEs allows the same shelf-stable biosensor chips to be used for multiple organism evaluations. Multiplex evaluation using EAMNPs with differing selective antibodies and non-selective attachment to the D-SPCE permits rinsing of the immobilized analytes on the biosensor surface (e.g., providing a means to eliminate non-conjugated Mab-EAMNPs or other potentially interfering substances from the biosensor surface prior to detection). The biosensor is fast, sensitive, and field-portable, having an estimated detection limit of 2 CFU/ml and a 2.5 hours of total testing time including PCR confirmation. The biosensor out performs the FDA BAM method in speed, field portability and cost and matches it in sensitivity and specificity. It provides a platform for extraction and concentration of microbial pathogens from food matrices, eliminating overnight enrichment steps, and it could be paired with nearly any rapid detection method for practical applications in food defense, food and water safety, and clinical diagnostics.

Because other modifications and changes varied to fit particular operating requirements and environments will be apparent to those skilled in the art, the disclosure is not considered limited to the example chosen for purposes of illustration, and covers all changes and modifications which do not constitute departures from the true spirit and scope of this disclosure.

Accordingly, the foregoing description is given for clearness of understanding only, and no unnecessary limitations should be understood therefrom, as modifications within the scope of the disclosure may be apparent to those having ordinary skill in the art.

Throughout the specification, where the compositions, processes, kits, or apparatus are described as including components, steps, or materials, it is contemplated that the compositions, processes, or apparatus can also comprise, consist essentially of, or consist of, any combination of the recited components or materials, unless described otherwise. Combinations of components are contemplated to include homogeneous and/or heterogeneous mixtures, as would be understood by a person of ordinary skill in the art in view of the foregoing disclosure.

What is claimed is:

1. A method for detecting the presence of a target analyte, the method comprising:
    (a) providing an analyte conjugate comprising: (i) a target analyte, (ii) a specific binding pair member bound to the target analyte, the specific binding pair member being capable of specifically binding to the target analyte, and (iii) a detection moiety bound to the specific binding pair member;
    (b) providing a biosensor comprising (i) a non-specific binding pair member immobilized on a working electrode of the biosensor, the non-specific binding pair member comprising a carbohydrate moiety capable of non-specific binding to the target analyte, and (ii) nanoparticles for enhancing conductivity immobilized on the working electrode of the biosensor;
    (c) immobilizing the analyte conjugate on the working electrode of the biosensor via non-specific binding between the target analyte of the analyte conjugate and the carbohydrate moiety of the non-specific binding pair member of the biosensor; and
    (d) detecting the detection moiety of the immobilized analyte conjugate.

2. The method of claim 1, wherein the carbohydrate moiety comprises a mannose moiety.

3. The method of claim 1, wherein the carbohydrate moiety is selected from the group consisting of monosaccharides, glycosides thereof, and combinations thereof.

4. The method of claim 1, wherein the carbohydrate moiety comprises at least one of a glucose moiety, a galactose moiety, a fucose moiety, a N-acetylgalactosamine moiety, a N-acetylglucosamine moiety, a mannose moiety, a rhamnose moiety, a N-Acetylneuraminic acid moiety, a glucuronic acid moiety, a galacturonic acid moiety, an arabinofuranose acid moiety, and a xylose moiety.

5. The method of claim 1, comprising replicating steps (a)-(d) in a multiplexed analysis for the detection of a plurality of different target analytes in a sample, wherein:
    (i) the target analyte, the specific binding pair member bound to the target analyte, and the corresponding analyte conjugate formed therefrom are different for each sample replicate in the multiplexed analysis; and (ii) the biosensor comprises the same carbohydrate moiety or moieties for each sample replicate in the multiplexed analysis.

6. The method of claim 1, wherein the non-specific binding pair member is immobilized on the working electrode via a stable covalent bond.

7. The method of claim 1, wherein the target analyte comprises a bacterium.

8. The method of claim 7, wherein:
(i) the bacterium is selected from the group consisting of *Escherichia, Bacillus, Staphylococcus, Klebsiella, Shigella, Pseudomona, Vibrio, Enterobacter,* species of the foregoing genera, and strains of the foregoing;
(ii) the specific binding pair member is capable of specifically binding to the selected bacterium; and
(iii) the carbohydrate moiety is capable of non-specific binding to a plurality of bacteria from the group.

9. The method of claim 1, wherein immobilizing the analyte conjugate in part (c) comprises contacting the analyte conjugate with the working electrode of the biosensor under conditions sufficient to non-specifically bind the carbohydrate moiety to the target analyte of the analyte conjugate.

10. The method of claim 1, further comprising washing the working electrode with the analyte conjugate immobilized thereon and prior to detecting the detection moiety.

11. The method of claim 1, wherein the detection moiety of the analyte conjugate comprises a conductive polymer moiety.

12. The method of claim 11, wherein detecting the detection moiety in part (d) comprises conductimetrically or electrochemically detecting the conductive polymer moiety of the analyte conjugate.

13. The method of claim 12, wherein, in part (c), the analyte conjugate is immobilized on the working electrode and adjacent a counter/reference electrode of an electrochemical biosensor device for performing conductimetric or electrochemical detection.

14. The method of claim 12, wherein, in part (c), the analyte conjugate is immobilized on the working electrode and between opposing electrodes of an electrochemical biosensor device for performing conductimetric or electrochemical detection.

15. The method of claim 1, wherein the detection moiety of the analyte conjugate comprises a conductive polymer shell bound to a magnetic nanoparticle core, the specific binding pair member being bound to the conductive polymer shell.

16. The method of claim 15, wherein:
(i) the magnetic nanoparticle comprises at least one of Fe(II) and Fe(III); and,
(ii) the conductive polymer is selected from the group consisting of polyanilines, polypyrroles, polythiophenes, derivatives thereof, combinations thereof, blends thereof with other polymers, and copolymers of the monomers thereof.

17. The method of claim 1, wherein:
(i) the detection moiety of the analyte conjugate comprises a conductive polymer nanoparticle, the specific binding pair member being bound to the conductive polymer nanoparticle; and
(ii) the analyte conjugate further comprises (A) a magnetic nanoparticle, and (B) an additional specific binding pair member bound to the magnetic nanoparticle and bound to the target analyte, the additional specific binding pair member being capable of specifically binding to the target analyte.

18. The method of claim 1, wherein the biosensor is a screen-printed carbon electrode (SPCE).

19. The method of claim 1, further comprising:
forming the analyte conjugate in a sample comprising the target analyte; and
determining that the target analyte is present in the sample.

20. The method of claim 1, wherein providing an analyte conjugate comprises:
(i) providing a sample comprising the target analyte;
(ii) providing an analyte probe comprising the specific binding pair member and the detection moiety bound to the specific binding pair member;
(iii) contacting the analyte probe with the sample under conditions sufficient to specifically bind the specific binding pair member to the target analyte, thereby forming the analyte conjugate; and
(iv) optionally separating the analyte conjugate from the sample prior to immobilizing the analyte conjugate on the working electrode of the biosensor.

21. The method of claim 1, wherein:
the carbohydrate moiety comprises a mannose moiety;
the target analyte comprises a bacterium;
the specific binding pair comprises an antibody capable of specifically binding to the bacterium;
the detection moiety of the analyte conjugate comprises a conductive polymer shell bound to a magnetic nanoparticle core, the specific binding pair member being bound to the conductive polymer shell;
the magnetic nanoparticle comprises at least one of Fe(II) and Fe(III); and,
the conductive polymer is selected from the group consisting of polyanilines, polypyrroles, polythiophenes, derivatives thereof, combinations thereof, blends thereof with other polymers, and copolymers of the monomers thereof.

22. The method of claim 1, wherein:
the nanoparticles for enhancing conductivity comprise gold nanoparticles, and
the nanoparticles are immobilized on the working electrode of the biosensor prior to immobilizing the analyte conjugate on the working electrode of the biosensor.

* * * * *